US012426897B2

(12) United States Patent
Lambert et al.

(10) Patent No.: US 12,426,897 B2
(45) Date of Patent: Sep. 30, 2025

(54) CALIBRATION AND ADJUSTMENT DETERMINATION OF A SURGICAL HANDPIECE SYSTEM

(71) Applicant: Stryker Corporation, Kalamazoo, MI (US)

(72) Inventors: Trevor Jonathan Lambert, Portage, MI (US); Adam Simon, Richland, MI (US); Brendan Schneider, Portage, MI (US); Rahul Sharma, Gurgaon (IN)

(73) Assignee: Stryker Corporation, Portage, MI (US)

( * ) Notice: Subject to any disclaimer, the term of this patent is extended or adjusted under 35 U.S.C. 154(b) by 1189 days.

(21) Appl. No.: 17/290,536

(22) PCT Filed: Nov. 1, 2019

(86) PCT No.: PCT/US2019/059463
§ 371 (c)(1),
(2) Date: Apr. 30, 2021

(87) PCT Pub. No.: WO2020/092951
PCT Pub. Date: May 7, 2020

(65) Prior Publication Data
US 2021/0378684 A1     Dec. 9, 2021

Related U.S. Application Data

(60) Provisional application No. 62/901,878, filed on Sep. 18, 2019, provisional application No. 62/754,944, filed on Nov. 2, 2018.

(51) Int. Cl.
*A61B 17/16*     (2006.01)
*A61B 17/00*     (2006.01)

(52) U.S. Cl.
CPC ...... *A61B 17/1622* (2013.01); *A61B 17/1633* (2013.01); *A61B 2017/00075* (2013.01); *A61B 2017/00725* (2013.01)

(58) Field of Classification Search
CPC .............. A61B 17/1615; A61B 17/162; A61B 17/1622; A61B 17/1633
See application file for complete search history.

(56) References Cited

U.S. PATENT DOCUMENTS

| | | | |
|---|---|---|---|
| 9,186,156 | B2 | 11/2015 | Xie |
| 9,204,885 | B2 | 12/2015 | McGinley et al. |

(Continued)

FOREIGN PATENT DOCUMENTS

| | | |
|---|---|---|
| CN | 103997963 A | 8/2014 |
| JP | 2011514196 A | 5/2011 |

(Continued)

OTHER PUBLICATIONS

International Search Report for Application No. PCT/US2019/059463 dated Nov. 27, 2020, 6 pages.

(Continued)

*Primary Examiner* — Si Ming Ku
(74) *Attorney, Agent, or Firm* — Howard & Howard Attorneys PLLC

(57) ABSTRACT

A surgical handpiece system capable of determining a suitable screw length for bone fixation with a bone plate that compensates an initial screw length value based on orientation of the surgical handpiece system during a drilling process. The surgical handpiece system comprising a surgical handpiece including a depth measurement extension and a sensor. The depth measurement extension may be configured to determine a thickness of bone when a drill bit is attached and used to drill through the bone. The sensor may be configured to generate an orientation signal responsive to orientation of the depth measurement extension. The surgical handpiece system also comprises a processor in communication with the sensor and configured to determine the suitable screw length for bone fixation based the sensor.

18 Claims, 25 Drawing Sheets

(56) References Cited

U.S. PATENT DOCUMENTS

| | | | |
|---|---|---|---|
| 9,662,179 B2* | 5/2017 | Nam | A61C 1/0023 |
| 10,231,742 B2 | 3/2019 | Lo et al. | |
| 2007/0088364 A1 | 4/2007 | Ruhling et al. | |
| 2009/0228047 A1 | 9/2009 | Derouet et al. | |
| 2009/0326537 A1 | 12/2009 | Anderson | |
| 2012/0310247 A1 | 12/2012 | Hsieh | |
| 2012/0319859 A1 | 12/2012 | Taub et al. | |
| 2014/0148808 A1 | 5/2014 | Inkpen et al. | |
| 2014/0257413 A1 | 9/2014 | Appenzeller et al. | |
| 2015/0201918 A1 | 7/2015 | Kumar et al. | |
| 2016/0015483 A1 | 1/2016 | Kumar et al. | |
| 2016/0120553 A1* | 5/2016 | Xie | A61B 17/1626 606/80 |
| 2016/0128704 A1 | 5/2016 | McGinley et al. | |
| 2016/0192948 A1 | 7/2016 | Wu et al. | |
| 2016/0256071 A1 | 9/2016 | Shelton, IV et al. | |
| 2017/0007328 A1 | 1/2017 | Cattin et al. | |
| 2017/0181753 A1 | 6/2017 | Langeland | |
| 2017/0209154 A1 | 7/2017 | Krause et al. | |
| 2018/0042619 A1 | 2/2018 | Frey et al. | |
| 2018/0242988 A1 | 8/2018 | Dacosta et al. | |

FOREIGN PATENT DOCUMENTS

| | | | |
|---|---|---|---|
| JP | 2018108267 A | 7/2018 | |
| KR | 20170106441 A | 9/2017 | |
| WO | 2012033823 A1 | 3/2012 | |
| WO | 2013044165 A2 | 3/2013 | |
| WO | 2017040783 A1 | 3/2017 | |
| WO | 2017083992 A1 | 5/2017 | |

OTHER PUBLICATIONS

Partial International Search Report for Application No. PCT/US2019/059463 dated Jun. 4, 2020, 2 pages.

Stryker, "CrossFlow Tubing Webpage", 1998-2021, https://www.stryker.com/us/en/sports-medicine/products/crossflow-tubing.html, 2 pages.

Vinmeo, "Stryker Sonopet Setup Video", https://vimeo.com/402638416, Apr. 2020, 2 pages.

Youtube, "CUSA Clarity System Setup", Mar. 3, 2017, https://www.youtube.com/watch?v=M5aCRYmCQYA, 3 pages.

English language abstract for CN 103997963 A extracted from espacenet.com database on Oct. 29, 2024, 2 pages.

English language abstract and machine-assisted English translation for JP 2018-108267 A extracted from espacenet.com database on Sep. 5, 2023, 12 pages.

English language abstract for JP 2011-514196 A extracted from espacenet.com database on Sep. 5, 2023, 2 pages.

English language abstract for KR 2017-0106641 A extracted from espacenet.com database on Aug. 19, 2025, 2 pages.

* cited by examiner

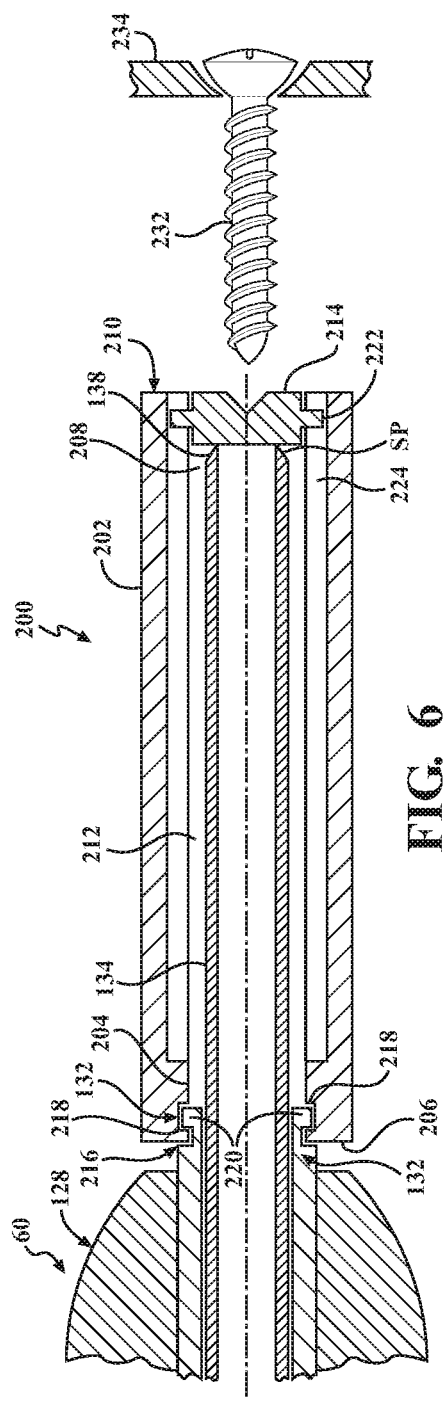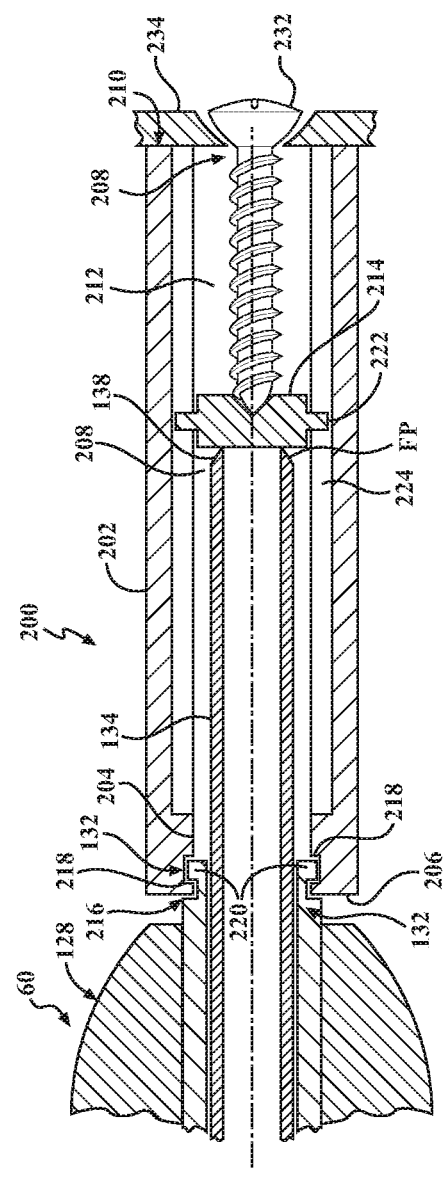

CALIBRATION AND ADJUSTMENT DETERMINATION OF A SURGICAL HANDPIECE SYSTEM

RELATED APPLICATIONS

The subject patent application is the National Stage entry of International Patent Application No. PCT/US2019/059463, filed Nov. 1, 2019, which claims priority to and all the benefits of U.S. Provisional Patent Application No. 62/754,944, filed on Nov. 2, 2018, and to U.S. Provisional Patent Application No. 62/901,878, filed on Sep. 18, 2019, the entire contents of which are hereby incorporated by reference.

BACKGROUND

Conventional medical and surgical procedures routinely involve the use of surgical tools and instruments which allow surgeons to approach and manipulate surgical sites. By way of non-limiting example, rotary instruments such as handheld drills are commonly utilized in connection with orthopedic procedures to address various musculoskeletal conditions, such as trauma, sports injuries, degenerative diseases, joint reconstruction, and the like. In procedures where handheld drills or similar surgical instruments are employed, rotational torque selectively generated by an actuator (e.g., an electric motor) is used to rotate a releasably-attachable drill bit or other surgical attachments at different speeds.

A surgical handpiece assembly drills bores in the tissue against which the drill bit is applied. One type of surgical procedure in which it is necessary to drill a bore is a trauma procedure to repair a broken bone. In this type of procedure, an elongated rod, sometimes called a nail, is used to hold the fractured sections of the bone together. To hold the nail in place, one or more bores are driven into the bone. These bores are positioned to align with complementary holes formed in the nail. A screw is inserted in each aligned bore and nail hole. The screws hold the nail in the proper position relative to the bone.

In another type of procedure, an implant known as a plate is secured to the outer surfaces of the fractured sections of a bone to hold the sections together. Screws hold the plate to the separate sections of bone. To fit a screw that holds a plate to bone it is necessary to first drill a bore to receive the screw.

As part of a procedure used to drill a screw-receiving bore in a bone, it is desirable to know the end-to-end depth of the bore. This information allows the surgeon to select size of screw that is fitted in the bore hole. If the screw is too short, the screw may not securely hold the nail into which the screw is inserted in place. If the screw is too long, the screw can extend an excessive distance out beyond the bone. If the screw extends an excessive distance beyond the bone, the exposed end of the screw can rub against the surrounding tissue. If this event occurs, the tissue against which the screw rubs is affected.

Accordingly, an integral part of many bone bore-forming procedures is the measuring of the depth of the bore. Currently, this measurement is often taken with a depth gauge separate from the drill. This requires the surgeon to, after withdrawing the drill bit from the bore, insert the depth gauge into the bore. Then, based on tactile feedback, the surgeon sets the gauge so the distal end of the gauge only extends to the far opening of the bore. Once these processes are complete, the surgeon reads the gauge to determine the depth of the bore.

It is desirable to identify methods and apparatus that improve these devices and methods.

SUMMARY

The present disclosure relates generally to a system for calibrating a surgical handpiece system capable of determining drill depth to an orthopedic implant set. An exemplary configuration provides a system including a surgical handpiece system. The surgical handpiece system includes a first housing and a depth measurement extension movably coupled to the first housing. A displacement sensor assembly is coupled to the first housing and configured to generate a signal responsive to displacement of the depth measurement extension. A calibration fixture is configured to engage the depth measurement extension of the surgical handpiece system to determine an adjustment of the orthopedic implant set. The calibration fixture has a second housing that defines a lumen that is configured to receive a surgical screw of the orthopedic implant set. The second housing has a proximal end configured to engage a distal surface of the first housing of the surgical handpiece system to axially constrain the second housing relative to the first housing. A slider is movably coupled to the second housing of the calibration fixture. The slider is configured to move axially relative to the second housing. The slider has a proximal surface configured to engage with the depth measurement extension of the surgical handpiece system. The slider also has a distal surface configured to engage with the surgical screw. The adjustment of the orthopedic implant set is determined based on the signal from the displacement sensor assembly and a nominal size of the surgical screw.

Another exemplary configuration provides a system for calibrating a surgical handpiece system capable of determining drill depth to an orthopedic implant set. The system includes a surgical handpiece system. The surgical handpiece system includes a housing and a depth measurement extension movably coupled to the housing. A displacement sensor assembly is coupled to a distal portion of the housing. The displacement sensor assembly is configured to generate a displacement signal responsive to movement of the depth measurement extension relative to the housing. A processor is configured to receive the signal from the displacement sensor assembly. A calibration fixture is configured to engage the distal portion of the housing of the surgical handpiece system to engage the depth measurement extension of the surgical handpiece system. One of the surgical handpiece system and the calibration fixture includes a presence sensor and the other of the surgical handpiece system and the calibration fixture includes an emitter. The presence sensor is configured to generate a signal responsive to presence of the emitter when the calibration fixture engages the distal portion of the housing of the surgical handpiece system. The processor is configured to receive the signal from the presence sensor and determine the calibration fixture is engaging the distal portion of the housing of the surgical handpiece system to operate the surgical handpiece system in a calibration mode. An adjustment of the orthopedic implant set is determined based on the signal from the displacement sensor assembly while the surgical handpiece system is in the calibration mode and on a nominal size of the surgical screw.

Yet another exemplary configuration provides a method of calibrating a surgical handpiece system capable of determining drill depth to an orthopedic implant set. The method including providing a surgical handpiece system including a first housing and a depth measurement extension movable relative to the first housing. The method also including providing a calibration fixture that includes a second housing defining a lumen and a slider movable relative to the second housing at least partially within the lumen. The method also including selecting a surgical screw having a certain nominal size from the orthopedic implant set. The method further including selecting a surgical plate to be used in an upcoming surgery from the orthopedic implant set. The method also including engaging the depth measurement extension of the surgical handpiece system with the slider of the calibration fixture. The method further including inserting the surgical screw through the surgical plate to engage a head of the surgical screw to abut the surgical plate. The method also including engaging the slider of the calibration fixture with the surgical screw. The method further including engaging a distal surface of the second housing with the surgical plate. The method also including depressing the depth measurement extension of the surgical handpiece system with the slider of the calibration fixture. The method further including determining an adjustment of the orthopedic implant set based on the nominal size of the surgical screw and a displacement of the depressed depth measurement extension to calibrate the surgical handpiece system.

Another exemplary configuration provides a method for calibrating a surgical handpiece system capable of determining drill depth to an orthopedic implant set. The method including providing a calibration fixture and a surgical handpiece system that includes a displacement sensor assembly. One of the calibration fixture and the surgical handpiece system includes a presence sensor. The other of the calibration fixture and the surgical handpiece system includes an emitter. The method also including engaging a distal portion of the surgical handpiece system with a proximal end of the calibration fixture. The method further including determining the calibration fixture is engaging the distal portion of the surgical handpiece system with the presence sensor. The surgical handpiece system entering a calibration mode responsive to the presence sensor detecting the emitter. The method also including determining displacement of a depth measurement extension of the surgical handpiece system while in calibration mode. The method further including determining an adjustment of the orthopedic implant set based on displacement of the depressed depth measurement extension during calibration mode.

Yet another exemplary configuration provides a system for calibrating a surgical handpiece system capable of determining drill depth to an orthopedic implant set. The system includes the surgical handpiece system. The surgical handpiece system includes a depth measurement extension configured to determine a thickness of bone when a drill bit is attached and used to drill through the bone. A calibration block is configured to engage with a depth gauge supplied with the orthopedic implant set to determine an adjustment of the orthopedic implant set. The calibration block includes a top surface having a curved profile designed to interface with a plate from the orthopedic implant set. The top surface defines one or more holes to receive the depth gauge. A bottom surface of the block includes a depression intended to temporarily hold a distal portion of the depth gauge.

Another exemplary configuration provides a surgical handpiece system to determine a suitable screw length for bone fixation with a bone plate that compensates an initial screw length value based on orientation of the surgical handpiece system during a drilling process. The surgical handpiece system includes a surgical handpiece assembly. The surgical handpiece assembly has a handpiece housing and a motor disposed within the handpiece housing and configured to generate torque. A depth measurement extension is movably coupled to the handpiece housing. A sensor is configured to generate an orientation signal responsive to orientation of the depth measurement extension. A drill bit is configured to be coupled to and receive torque from the motor of the surgical handpiece assembly. A processor is configured to receive the signals from the sensor and determine the suitable screw length for bone fixation based on signals from the sensor.

BRIEF DESCRIPTION OF THE DRAWINGS

FIG. 6 is a sectional view of a calibration fixture interfacing with the distal end of the surgical handpiece system.

FIG. 7 is the same calibration fixture from FIG. 6 with all components aligned and compressed.

DETAILED DESCRIPTION

Figure 1:
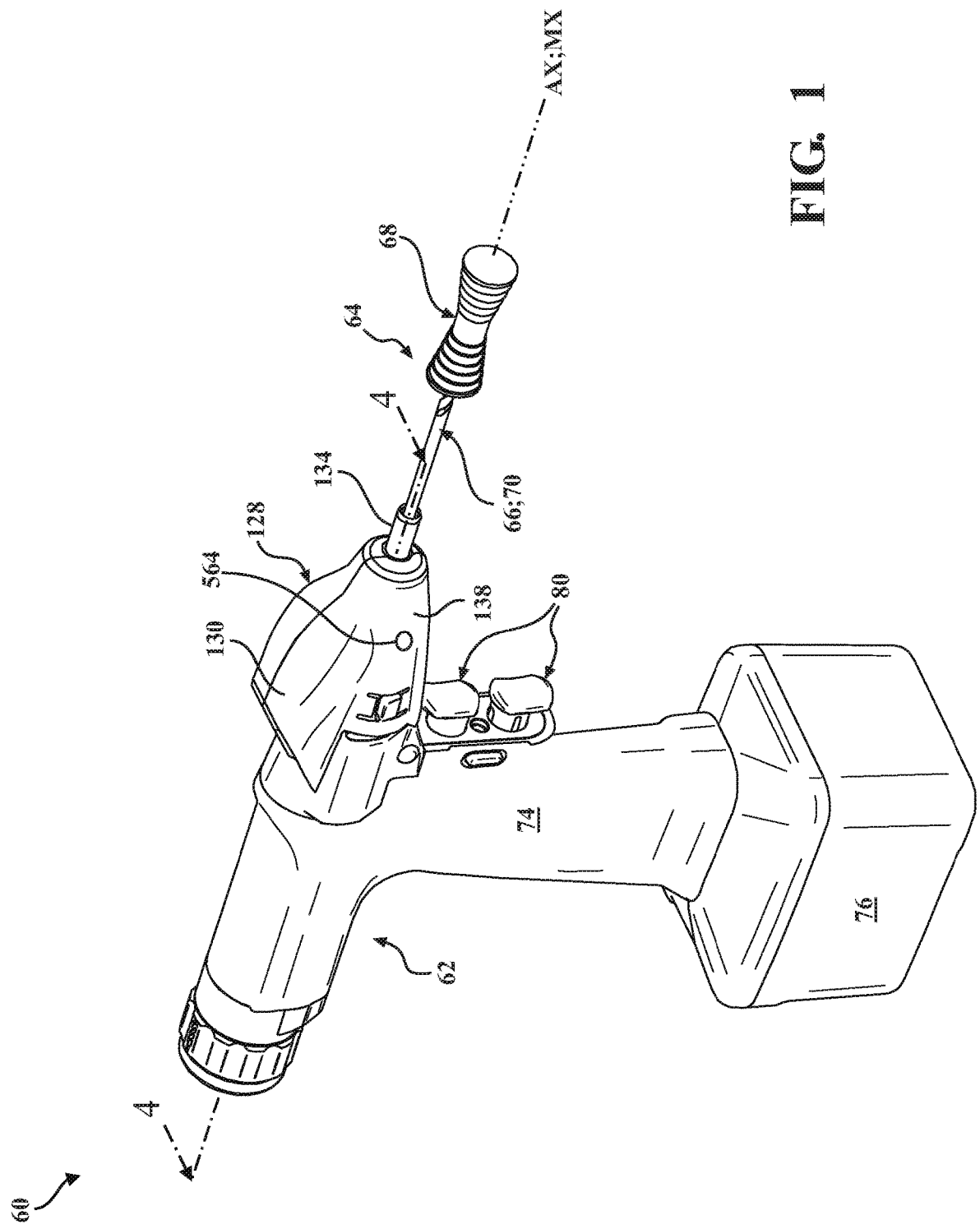
FIG. 1 is perspective view of a surgical handpiece system comprising a surgical handpiece assembly and a measurement module, the surgical handpiece assembly shown having a drill bit and a tip protector according to one configuration.
Figure 2:
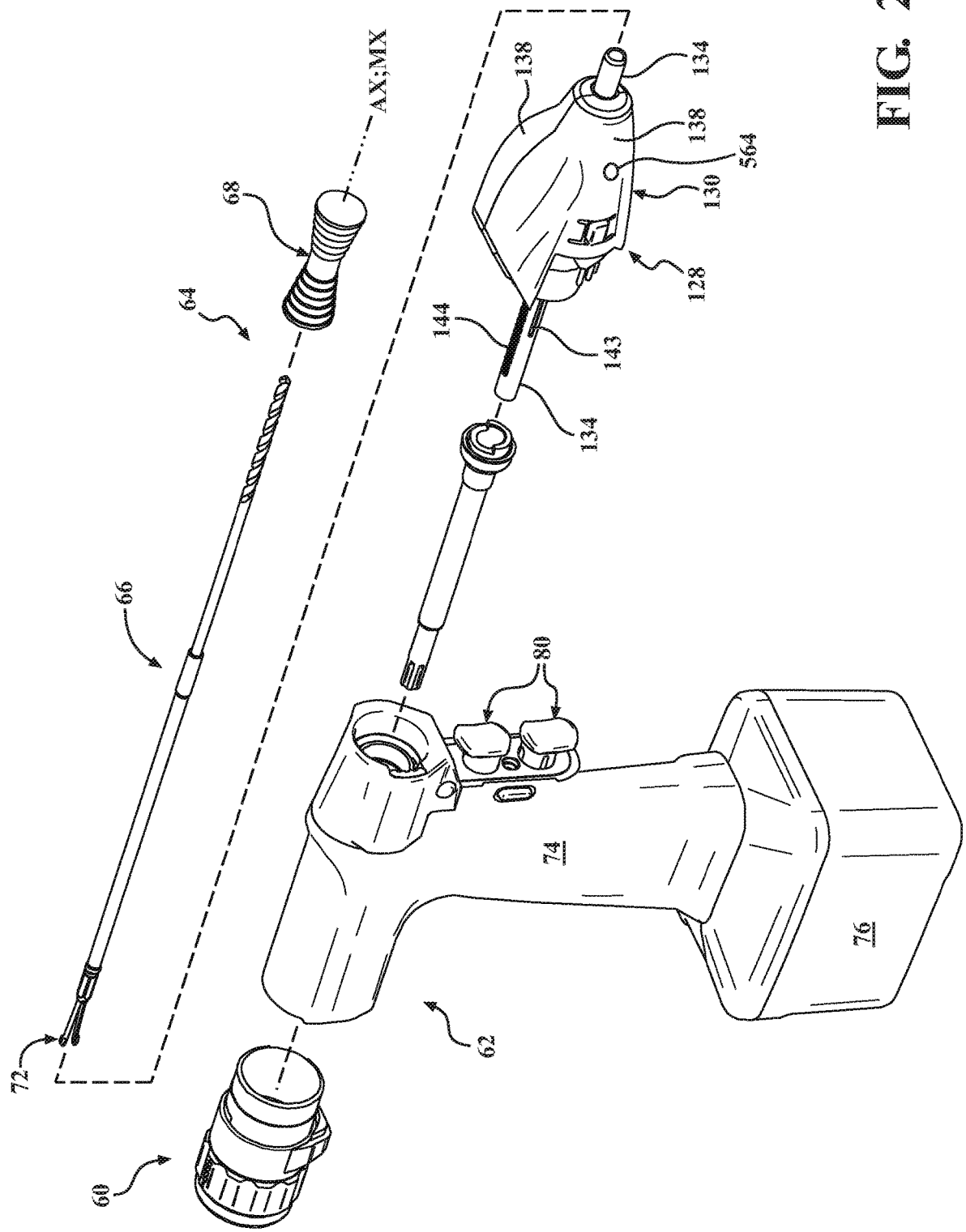
FIG. 2 is a partially-exploded perspective view of the surgical handpiece system of FIG. 1, with the surgical handpiece system shown having a measurement module, a drive cannula, and a release assembly spaced from a handpiece housing assembly, and with the end effector assembly removed from the surgical handpiece assembly and shown with the tip protector spaced from a distal cutting tip portion of the drill bit.

With reference to the drawings, where like numerals are used to designate like structure throughout the several views, a surgical handpiece system is shown at 60 in FIGS. 1-2 for performing an operational function associated with medical and/or surgical procedures. In the representative configuration illustrated herein, the surgical handpiece system 60 is employed to facilitate penetrating tissue of a patient, such as bone. To this end, the illustrated configuration of the surgical handpiece system 60 comprises a surgical handpiece assembly 62 and an end effector assembly, generally indicated at 64. The end effector assembly 64, in turn, comprises a drill bit 66 and a tip protector 68. As is best depicted in FIG. 2, the drill bit 66 extends generally longitudinally along an axis AX between a cutting tip portion, generally indicated at 70, and an insertion portion, generally indicated at 72. As is described in greater detail below, the cutting tip portion 70 is configured to engage tissue, and the insertion portion 72 is configured to facilitate releasable attachment of the drill bit 66 to the surgical handpiece assembly 62.

In order to help facilitate attachment of the drill bit 66 to the surgical handpiece assembly 62, in some configurations, the tip protector 68 is configured to releasably secure to the cutting tip portion 70 of the drill bit 66 while concealing at least a portion of the cutting tip portion 70 of the drill bit 66, thereby allowing a user (e.g., a surgeon) of the surgical handpiece system 60 to handle and position the drill bit 66 safely during attachment to the surgical handpiece assembly 62. Once the end effector assembly 64 has been attached to the surgical handpiece assembly 62, the tip protector 68 is subsequently removed from the cutting tip portion 70 of the drill bit 66, and the surgical handpiece system 60 can then be utilized to penetrate tissue.

A variety of different orthopedic implant sets, which can include screws, plates, nails, or pins along with a depth gauge, may be used from various manufacturers, each implant set may include a variety of different screws with a nominal identification of screw length. The depth gauge accompanying an orthopedic implant set is configured to measure the bore depth and provide a user a measurement that corresponds to the nominal screw length in that orthopedic implant set. The depth gauge accounts for items like the thickness of the plate and how the manufacturer determines screw length, e.g. with or without the thickness of the screw head. The difference between the thickness of the bone and the nominal screw length is referred to as an adjustment.

Referring now to FIGS. 1-4, in the representative configuration illustrated herein, the surgical handpiece assembly 62 is realized as a handheld drill with a pistol-grip shaped handpiece housing assembly 74 which releasably attaches to a battery 76 (battery attachment not shown in detail). However, it is contemplated that the handpiece housing assembly can have any suitable shape with or without a pistol grip. While the illustrated surgical handpiece assembly 62 employs a battery 76 which is releasably attachable to the handpiece housing assembly 74 to provide power to the surgical handpiece assembly 62 utilized to rotate the drill bit 66, it will be appreciated that the surgical handpiece assembly 62 may be configured in other ways, such as with an internal (e.g., non-removable) battery, or with a tethered connection to an external console, power supply, and the like. Other configurations are contemplated.

In the illustrated configuration, the battery 76 or other power source provides power to a controller 78 which, in turn, is disposed in communication with a user input device 80 and an actuator assembly 82. The user input device 80 and the actuator assembly 82 are each supported by the handpiece housing assembly 74. The controller 78 is generally configured to facilitate operation of the actuator assembly 82 in response to actuation of the user input device 80. The user input device 80 is shown as a trigger-style configuration in the illustrated configuration, is responsive to actuation by a user (e.g., a surgeon), and communicates with the controller 78, such as via electrical signals produced by magneto-resistive sensors (e.g., Hall effect sensors) and magnets. Thus, when the surgeon actuates the user input device 80 to operate the surgical handpiece assembly 62, the controller 78 directs power from the battery 76 to the actuator assembly 82 which, in turn, generates rotational torque employed to rotate the drill bit 66 or other surgical end effector, as described in greater detail below. Those having ordinary skill in the art will appreciate that the handpiece housing assembly 74, the battery 76, the controller 78, and the user input device 80 could each be configured in a number of different ways to facilitate generating rotational torque without departing from the scope of the present disclosure.

Figure 3:
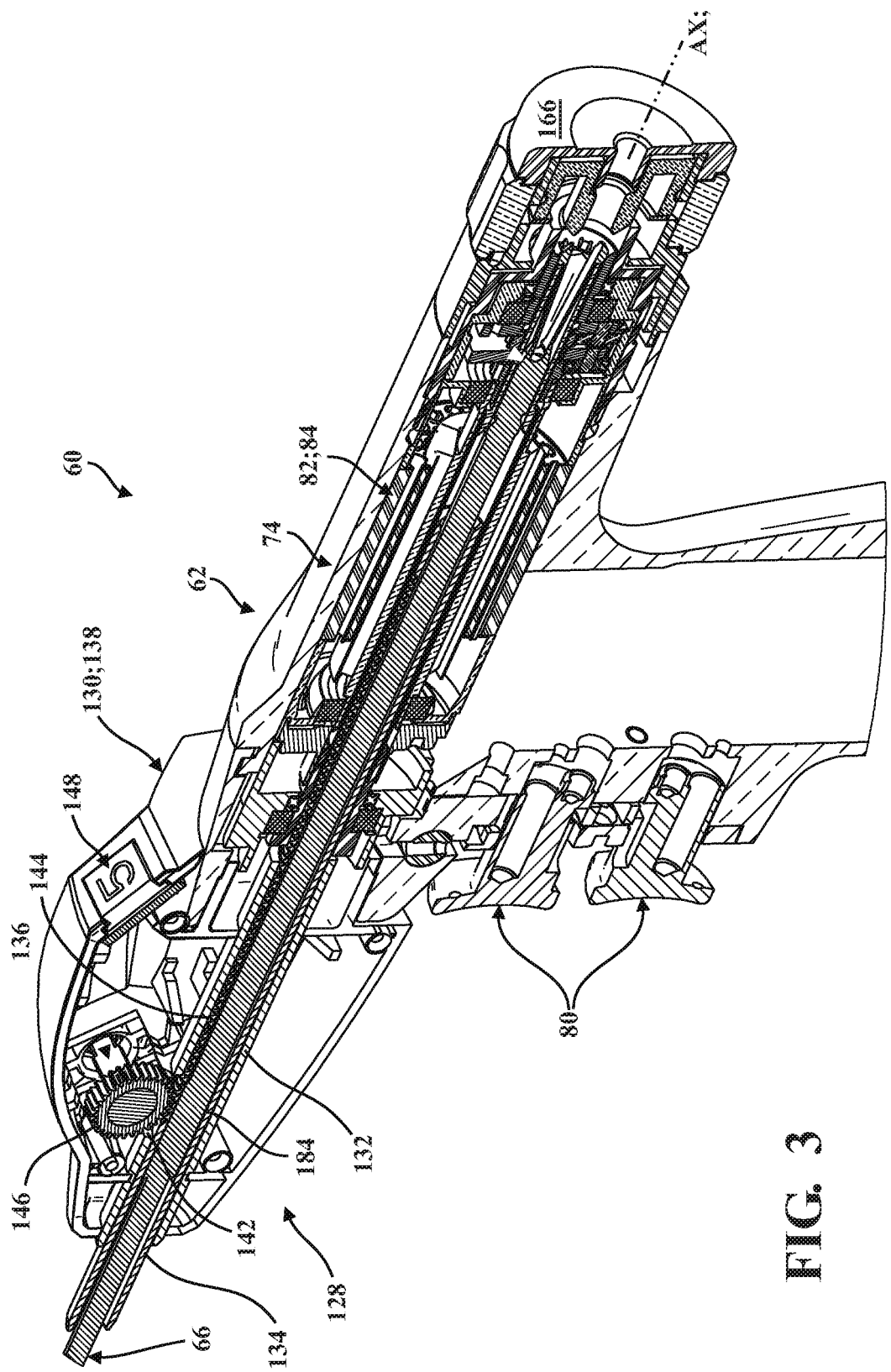
FIG. 3 is a partial isometric sectional view taken along line 4-4 in FIG. 1.
Figure 4:
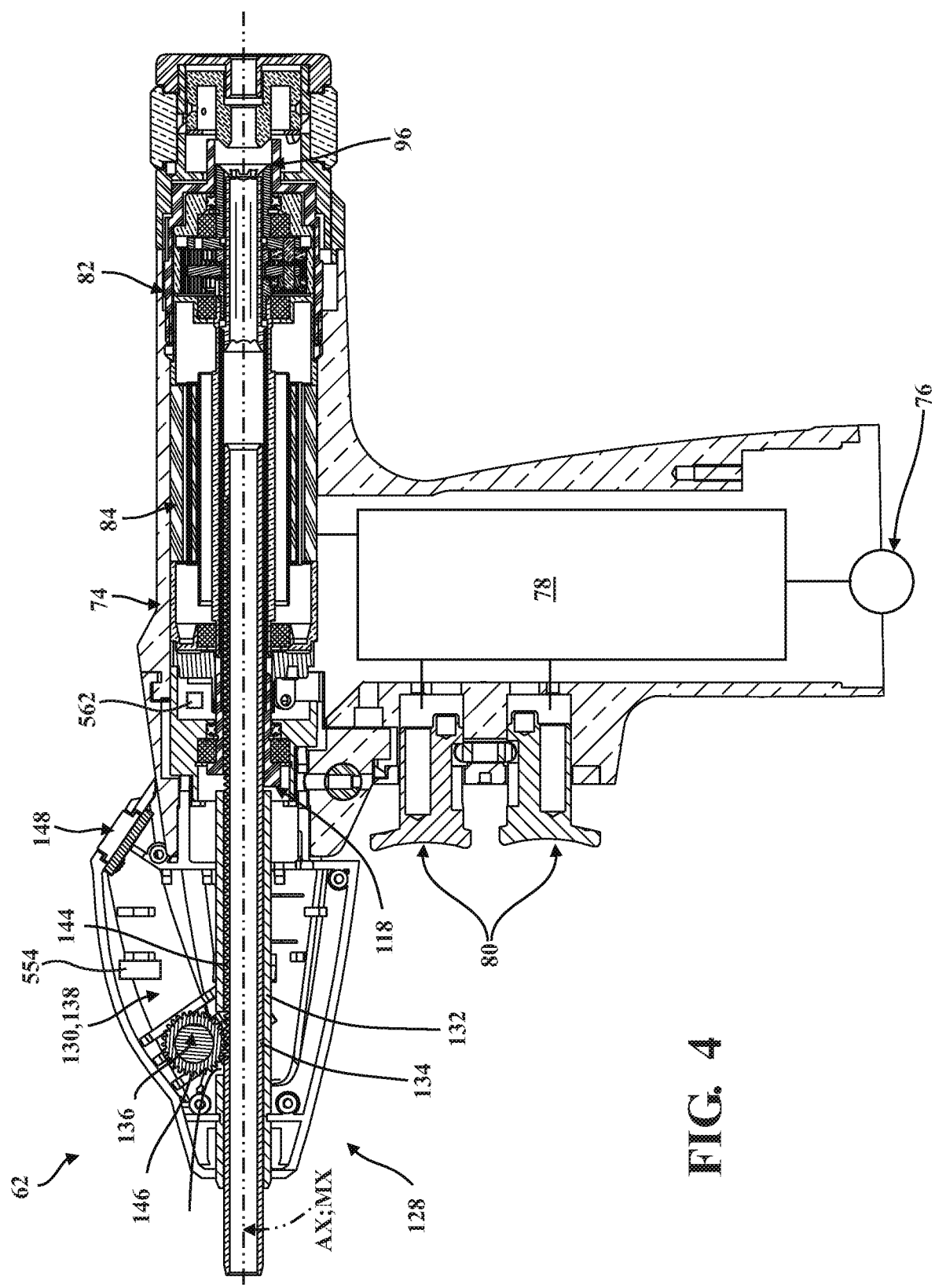
FIG. 4 is a sectional view taken longitudinally through the surgical handpiece assembly of FIGS. 1-2, with the end effector assembly removed from the surgical handpiece assembly.

Referring now to FIGS. 1-4, the illustrated configuration of the surgical handpiece system 60 further comprises a measurement module, generally indicated at 128, which may be optionally configured to releasably attach to the surgical handpiece assembly 62 to provide the surgeon with measurement functionality during use. To this end, and as is shown in FIGS. 3 and 4, the measurement module 128 generally comprises a module housing 130, a guide bushing 132, a depth measurement extension 134, a displacement sensor assembly 136, and a rotatable gear 146. In some configurations, the module housing 130 is releasably attachable to the handpiece housing assembly 74. In other configurations, the measurement module 128 is releasably attached to the surgical handpiece assembly 62 in another manner. In certain configurations, the measurement module 128 may include one or more buttons for controlling a function of the measurement module 128. The module housing 130 generally supports the various components of the measurement module 128. In still other configurations, the surgical handpiece assembly 62 and the measurement module 128 are not releasably attached to each other. Instead, the surgical handpiece assembly 62 and the measurement module 128 form one integral assembly such that the module housing 130 forms a portion of the handpiece housing assembly 74.

The depth measurement extension 134 is disposed within the guide bushing 132 and is supported for translational movement along a measurement axis MX. When the measurement module 128 is attached to the surgical handpiece assembly 62, the measurement axis MX is arranged to be coaxial with the axis AX. An elongated recessed slot 143 (partially depicted in FIG. 2) is optionally formed transversely into the depth measurement extension 134 and extends longitudinally.

The depth measurement extension 134 further comprises a plurality of rack teeth 144 disposed linearly along at least a partial length of the depth measurement extension 134 which are disposed in meshed engagement with the gear 146 arranged adjacent a distal end of the guide bushing 132. As shown in FIG. 4, the window 142 of the guide bushing 132 is arranged adjacent to the gear 146 to facilitate the meshed engagement between the rack teeth 144 and the gear 146 such that rotation of the gear 146 and movement of the depth measurement extension 134 are directly proportional. The displacement sensor assembly 136 is responsive to rotation of the gear 146 resulting from axial movement of the depth measurement extension 134, and may be realized with a potentiometer 147 (shown in FIG. 5), a rotary encoder, and the like, in order to generate electrical signals representing changes in the position of the depth measurement extension 134 along the measurement axis MX. Thus, it will be appreciated that the displacement sensor assembly 136 is able to provide the surgical handpiece system 60 with enhanced functionality. By way of example, in some configurations, the displacement sensor assembly 136 may be disposed in communication with the controller 78, which may be configured to interrupt or adjust how the motor 84 is driven based on movement of the depth measurement extension 134, such as to slow rotation of the drill bit 66 at a specific drilling depth into tissue. In some configurations, the controller 78 may be disposed in the measurement module 128. In still other configurations, the displacement sensor assembly 136 may be disposed in communication with a sub-controller (not shown) of the measurement module 128 and the sub-controller may be disposed in communication with the controller 78. The displacement sensor assembly 136 may also be disposed in communication with a display 148, such as a display screen, one or more light-emitting diodes (LEDs), and the like, to provide the surgeon with information relating to movement of the depth measurement extension 134, such as to display a real-time drilling depth, a recorded historical maximum drilling depth, and the like. Other configurations are contemplated. This same information may also be communicated to the user with a speaker to provide audio indications of the real-time drilling depth, a recorded historical maximum drilling depth, and the like. The disclosure of International Patent Publication No. WO/2017/040783 entitled "Powered Surgical Drill With Integral Depth Gauge That Includes A Probe That Slides Over A Drill Bit" and filed on Sep. 1, 2016, which was previously incorporated by reference in its entirety.

Various components of the measurement module 128 could be arranged in a number of different ways. Moreover, while the illustrated measurement module 128 attaches to the illustrated surgical handpiece assembly 62 and is compatible with the calibration fixtures 200, 300, 400, 500, 1300, 1500 of the present disclosure, it is contemplated that the surgical handpiece system 60 could omit the measurement module 128 in some configurations, such as to employ different types of modules, housings, covers, and the like. The measurement module 128 may also be affixed to the surgical handpiece assembly 62 in a different location and may be detachable or may be a permanent part of the surgical handpiece assembly 62. In configurations where the measurement module 128 is not attached to the distal end of the surgical handpiece assembly 62, components described or depicted herein as abutting the measurement module 128 may instead abut the surgical handpiece assembly 62. Further, while the depth measurement extension 134 is illustrated as a cannula it could instead partially enclose the drill bit 66, or the depth measurement extension 134 could be parallel to and offset from the drill bit 66. In other words, any device that includes a depth measurement extension 134 may be compatible with the devices and methods described herein.

Figure 5:
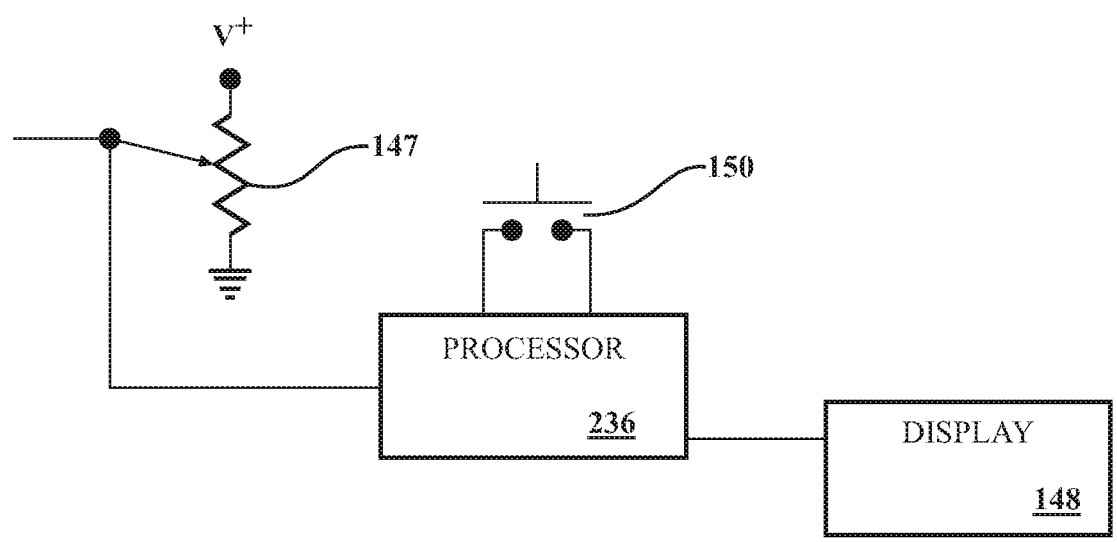
FIG. 5 is a block and partial schematic diagram of some of the signal processing components of the surgical handpiece system.

FIG. 5 depicts the basic electrical components of surgical handpiece system 60 that, based on position of the depth measurement extension 134, provide an indication of the depth of the bore formed by the drill bit 66. Not identified are the voltage regulating components that ensure the drive signals of the appropriate potentials are supplied to the bore depth displaying components. The components that provide the information about bore depth include the potentiometer 147. A voltage is applied to one end of the potentiometer 147. The opposed end of the potentiometer 147 is tied to ground. The voltage present at the wiper of the potentiometer 147 is applied to a processor 236. Also shown attached to the processor 236 is a zeroing switch 150. In the zeroing switch 150 may be mounted to the display 148.

Figure 12:
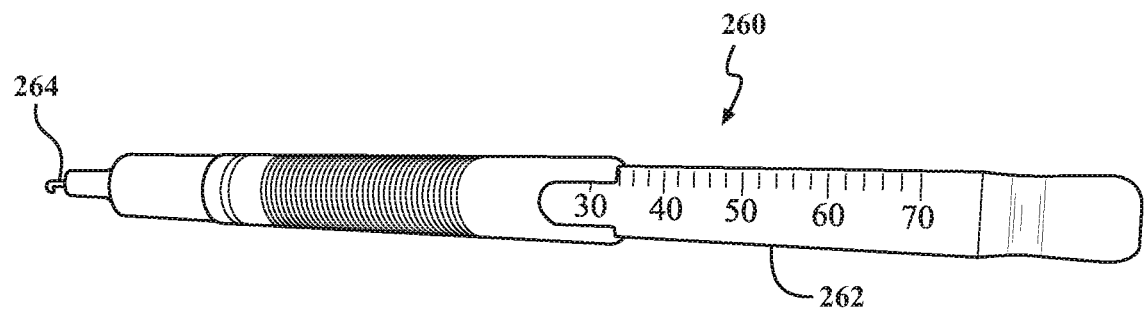
FIG. 12 is a perspective view of a depth gauge.

Each set of plate(s) 234 and screws 232 may provide a nominal screw length to identify the various screw sizes within the set. The nominal screw length provided for any particular set of plate(s) 234 and screws 232 does not necessarily correspond to any consistent metric. The nominal screw length could be the actual screw length with or without the screw head. The nominal screw length may or may not take into account the thickness of the plate 234 that the screw will ultimately be used with. To ensure that the surgeon correctly selects a screw 232 that is appropriate for the particular surgical procedure, a manufacturer-specific depth gauge 260 (See, e.g. FIG. 12) is provided with each set of plates 234 and screws 232.

Figure 13:
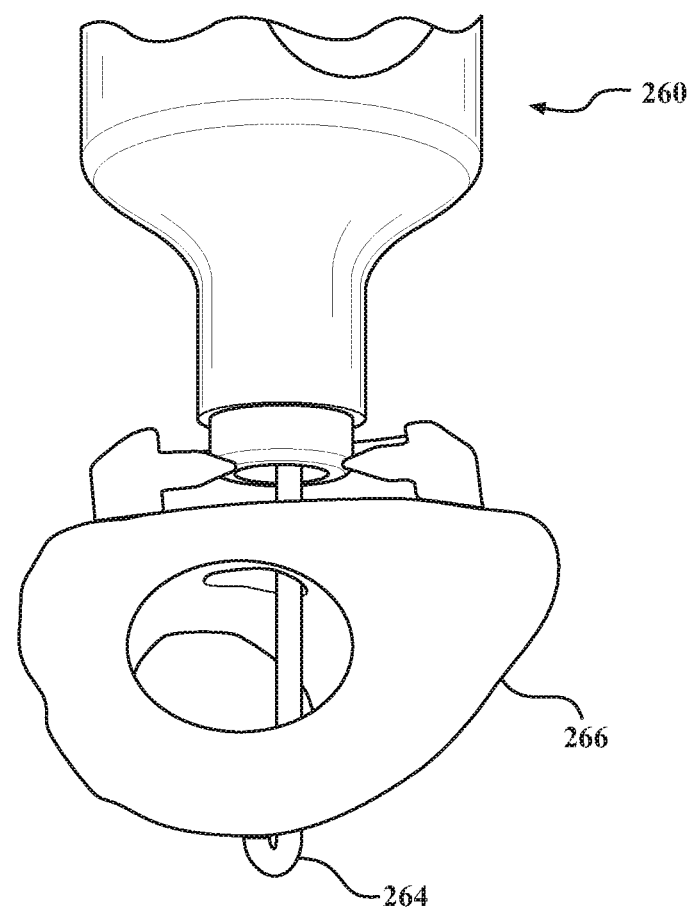
FIG. 13 is a perspective view of a depth gauge being used to measure the cortex to cortex thickness of an artificial bone.
Figure 14:
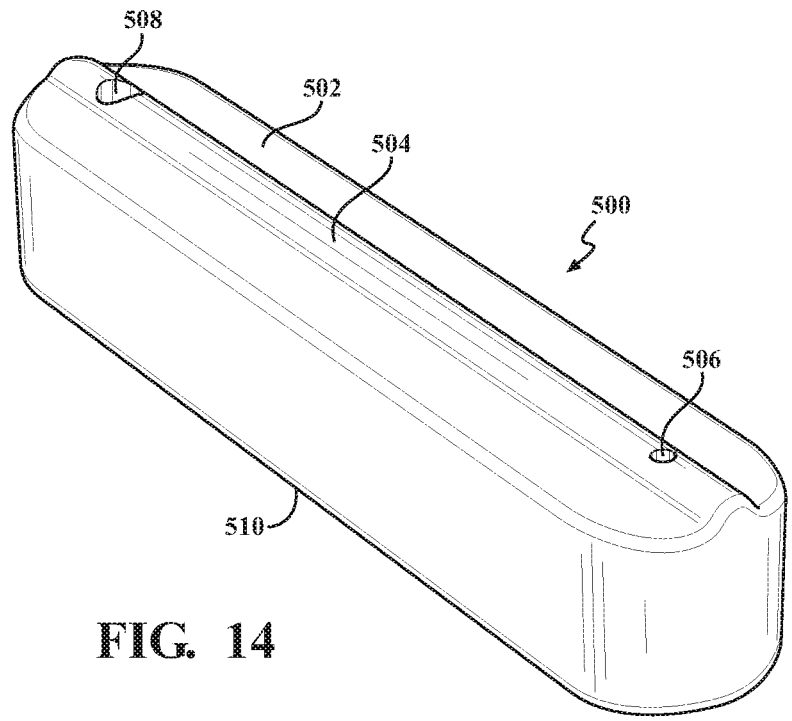
FIG. 14 is a perspective view of the top surface of a calibration block.
Figure 15:
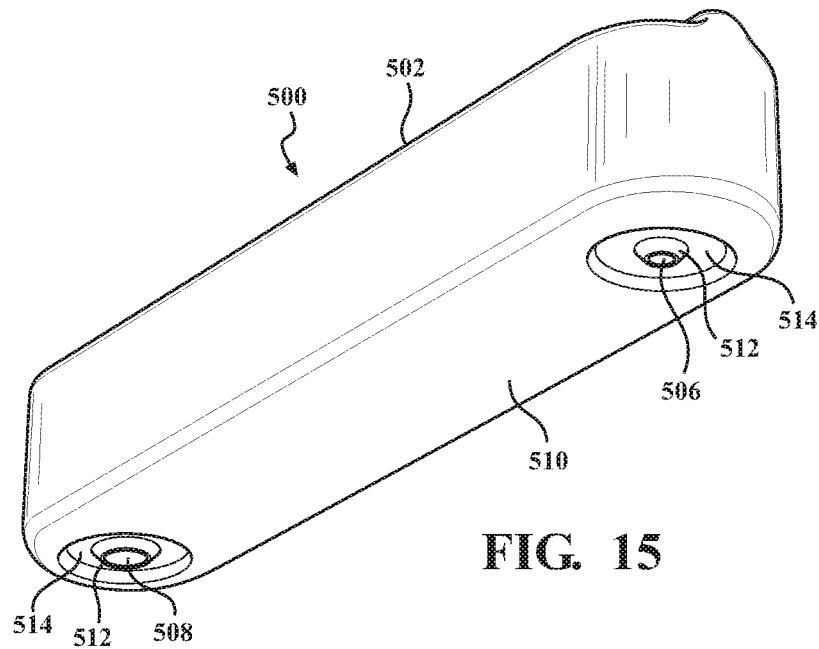
FIG. 15 is a perspective view of the bottom surface of a calibration block.

The depth gauge 260 is used to measure thickness of a bone 266, as shown in FIG. 13, and the measurement markings 262 on the depth gauge 260 associated with a given set correspond to the nominal screw length of the screws 232 provided with the set.

In order for the surgical handpiece system 60 to provide sufficient information to enable selection of the screw 232, the surgical handpiece system 60 must be calibrated to work with any one of over 1,300 different plate 234 and screw 232 sets. As will be described below, the surgical handpiece system 60 may be calibrated using a plate 234 and screw 232 provided with a particular implant set 230 or with a depth gauge 260 provided with the implant set 230.

A system for calibrating a surgical handpiece system 60 is shown in FIGS. 6 and 7. In this system, a screw 232 and plate 234 from the set are used in conjunction with the measurement module 128 and a calibration fixture 200 to calibrate the measurement module 128 for the surgical handpiece system 60.

In this system, the calibration fixture 200 has an elongated housing 202, such as a tubular or rectangular housing, with a proximal end opening 204 on a proximal end 206 and distal end opening 208 on a distal end 210. The housing 202 defines a lumen 212.

The housing 202 contains a slider 214 that is freely moveable in the lumen 212 of the housing 202 in the axial directions. The proximal face 226 of the slider 214 is designed to abut a distal end 138 of the depth measurement extension 134 of the measurement module 128. The distal face 228 of the slider 214 is designed to engage the tip of the selected screw 232.

In order to use the system in in FIGS. 6 and 7, the depth measurement extension 134 may be fully extended from the measurement module 128. The housing 202 is placed over the depth measurement extension 134 such that the depth measurement extension 134 is disposed within lumen 212. Furthermore, the proximal end 206 of the housing 202 is either pressed against the end of the measurement module 128 or may be secured to the measurement module 128 using an interlocking mechanism 216. While the interlocking mechanism is shown here as an interlocking recess 218 and protrusion 220, it should be appreciated that the interlocking mechanism may also take other suitable forms.

The slider 214 of the calibration fixture 200 is situated at the distal region of the calibration fixture 200 and abuts the extended depth measurement extension 134, referred to as starting point SP. The slider 214 is configured to move axially within the lumen 212 of the housing 202. The precise movement of the slider 214 may be guided by wings 222 which may be seated within corresponding sized grooves 224 within the housing 202 to ensure smooth motion relative to the longitudinal axis of the lumen. The slider 214 may alternatively interact with the housing 202 in other ways to ensure smooth motion within the lumen 212 of the housing 202.

The user actuates one or more user inputs on the measurement module 128 or surgical handpiece assembly 62 to operate the measurement module 128 in a calibration mode. This zeroes the measurement module 128. The user then selects a screw 232 of any length and a plate 234 from the set to be used. The plate 234 is placed against the distal end 210 of the calibration housing 202 and the screw 232 is inserted through the distal opening 208 of the plate 234 into the distal end 210 of the calibration fixture 200. The end of the screw 232 displaces the slider 214 and depth measurement extension 134 such that the slider 214 rests at a final position, FP, as shown in FIG. 7. The display 148 of the measurement module 128 may show the resulting displacement of the measurement extension.

In the example in FIGS. 6 and 7, the user selected a 26 mm screw, which displaced the depth measurement extension 134 by 23 mm. This displacement correlates to the cortex-to-cortex bone thickness that the surgical handpiece system 60 measures. The difference (3 mm) between the labelled length of selected screw 232 (26 mm) and the measured displacement (23 mm) is the length adjustment for this particular screw 232 and plate 234 set. The user may then enter a "Calibration Mode," which allows the length adjustment to be entered into the measurement module 128 and to be stored within a memory unit of the measurement module 128 for the remainder of the surgical case.

The user may then enter "Drilling Mode" through actuation of one or more user inputs on the surgical handpiece system 60. While in Drilling Mode, the stored adjustment will be automatically added to the live depth measurement and the measured cortex-to-cortex value determined by the measurement module 128 when the user drills through bone of the patient. This technique effectively bridges the gap between the absolute measurement of the bone thickness and proper screw selection for a given system. Alternatively, the adjustment may be retained by the user to enable proper screw 232 selection. In other words, the user will know that he or she will need to add 3 mm to the measurement determined by the measurement module 128 when determining the appropriate screw length to be used.

Figure 8:
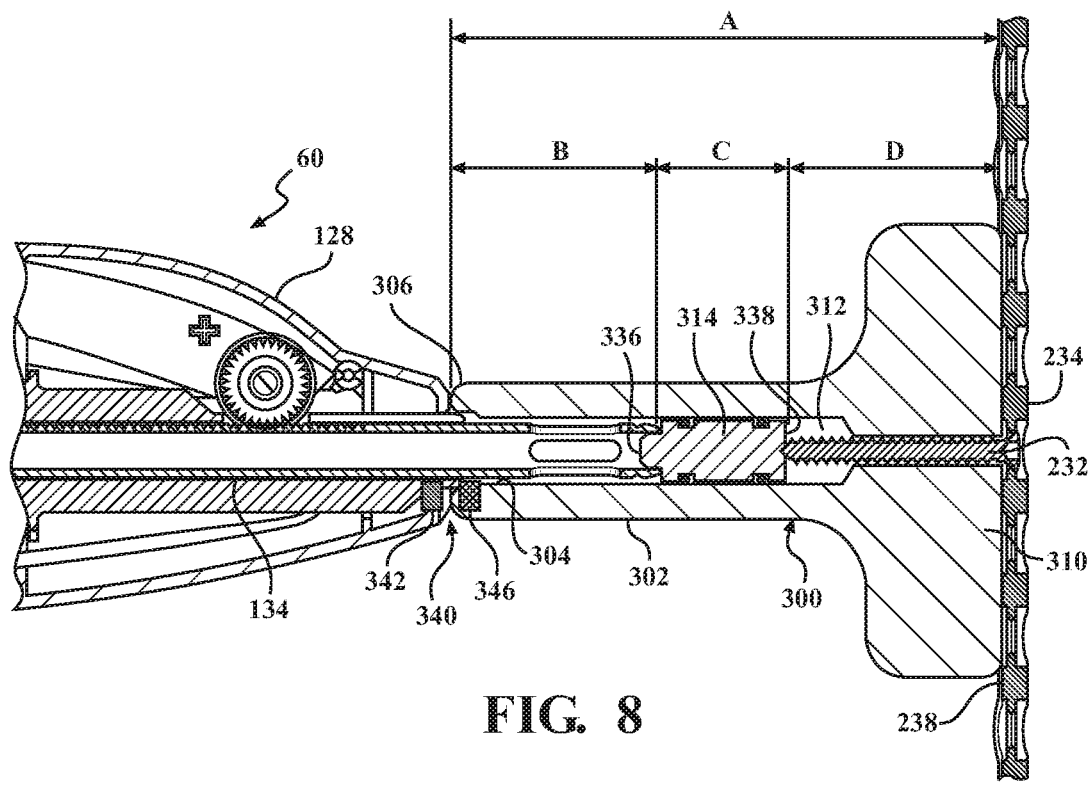
FIG. 8 is a sectional view taken longitudinally showing a calibration fixture for automatic calibration of a surgical handpiece system.
Figure 9:
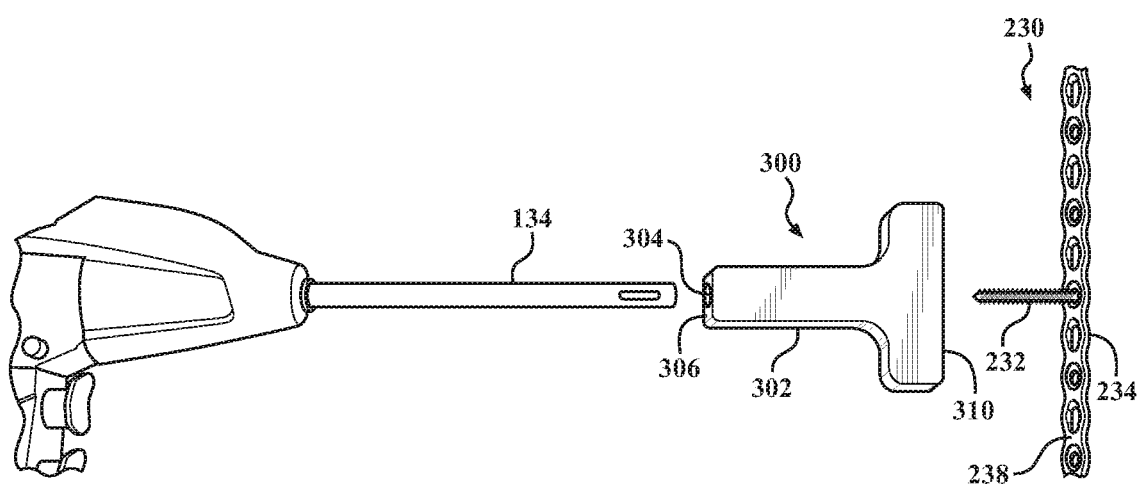
FIG. 9 is a perspective view of a calibration fixture for automatic calibration of a surgical handpiece system prior to calibration.
Figure 10:
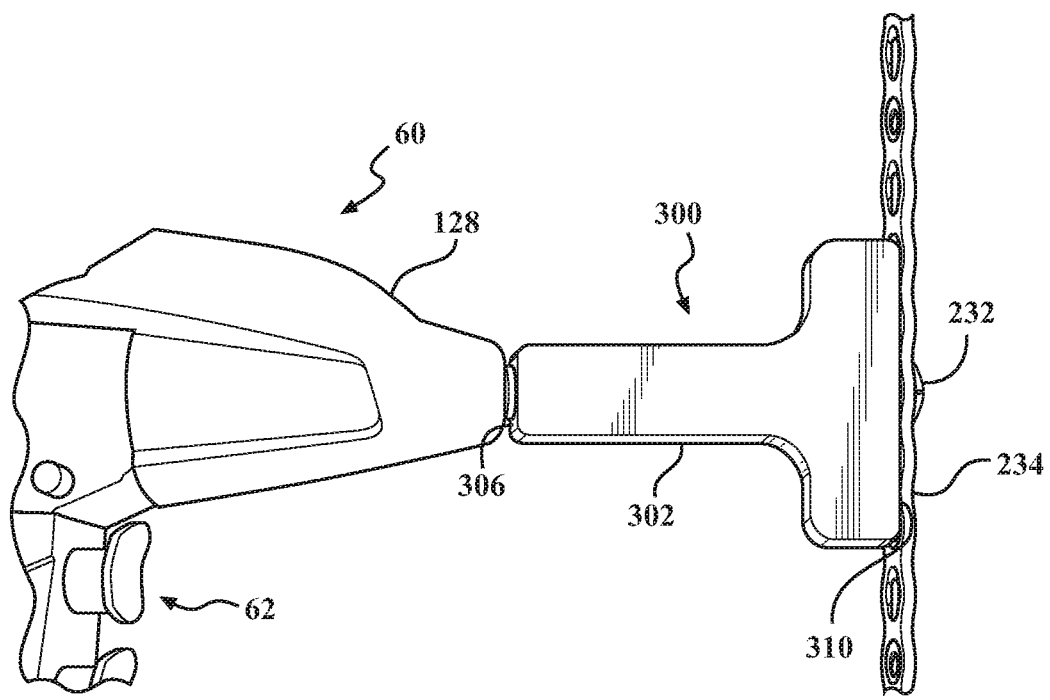
FIG. 10 is a perspective view of a calibration fixture for automatic calibration of a surgical handpiece system during calibration.

FIGS. 8, 9, and 10 show another calibration system that uses a surgical handpiece system 60 having the measurement module 128 interfacing with an alternative design of the calibration fixture 300, with screw 232, and plate 234 from a set to calibrate the surgical handpiece system 60. Several changes and additions have been made to the system and method shown in FIGS. 6 and 7.

The calibration fixture 300 is shown with a T-shaped housing 302. The T-shaped housing 302 provides an ergonomic benefit when holding the calibration fixture 300. The T-shape also provides more surface area for the plate 234 to rest against.

The surgical handpiece system 60 and the calibration fixture 300 may comprise a calibration sensor assembly 340. Sensor 342 is included in the measurement module 128. The sensor 342 may be coupled to a processor within the measurement module 128 or the surgical handpiece assembly 62. The processor 236, based on the input signal from the sensor 342, is configured to determine whether the calibration fixture 300 is positioned proximate to the surgical handpiece system 60. The sensor assembly 340 may include a second component, such as an emitter, located in the calibration fixture 300 and configured to emit a signal to the sensor 342. When the processor 236 determines that the calibration fixture 300 is positioned proximate to the measurement module 128, the processor may cause the measurement module 128 to automatically enter the Calibration Mode. It should be appreciated that the processor may be tuned such that the processor only determines that the calibration fixture 300 is proximate when the calibration fixture 300 is less than a predetermined distance away from the measurement module 128, such as less than 1 mm. In other configurations, the processor may be tuned such that the processor only determines that the calibration fixture 300 is abutting the measurement module 128. In other configurations, the processor may cause the measurement module 128 to automatically enter the Calibration Mode when the measurement module 128 first receives power from the surgical handpiece assembly 62 or another portion of the surgical handpiece system 60.

In one potential implementation, the sensor 342 comprises a magneto-resistive sensor. The sensor 342 may be positioned near the distal end of the measurement module 128 or surgical handpiece assembly 62. The calibration fixture 300 may include an emitter 346 such as a magnet positioned near the proximal end 306 of the calibration fixture 300. It is contemplated that the sensor assembly 340 may take other suitable forms to detect the proximity of the calibration fixture 300, for example, the sensor 342 may take the form of a mechanical button or switch that is depressed, an RFID antenna that is triggered by a coil included on the calibration fixture 300, or a capacitive sensor, or a hall effect sensor.

It is also contemplated that a plurality of emitters 346 may be arranged near the proximal end of the calibration fixture 300 to permit the sensor 342 to detect one or more of the plurality of emitters 346 when the calibration fixture 300 is proximate the measurement module. This feature is advantageous because the calibration fixture 300 may be radially oriented in a number of different positions relative to the measurement module 128 and the sensor 342 may still determine the calibration fixture 300 is proximate the measurement module 128. In one configuration, an array of emitters 346 may be arranged about a proximal opening of the calibration fixture 300 that is configured to receive the depth measurement extension 134. The array of emitters 346 may be circumferentially spaced such that the sensor 342 may detect the calibration fixture is proximate in any radial orientation of the calibration fixture 300 relative the measurement module 128.

In other configurations, the sensor 342 may be coupled to the calibration fixture 300 near the proximal end of the calibration fixture 300 and the emitter 346 may be coupled to the measurement module 128 near the distal end of the module housing 130.

Once the processor determines that the calibration fixture 300 is positioned proximate to the surgical handpiece system 60 based on the sensor 342 input signal, the processor may cause the measurement module 128 or surgical handpiece assembly 62 to enter calibration mode. Then—once measurement module 128 determines the length adjustment for a given plate 234 and screw 232 set through the procedure described for the system shown in FIGS. 6 and 7 and the measurement module 128 stores length adjustment in the memory unit of the measurement module 128—the user reenters the Drilling Mode. During the Drilling Mode the length adjustment may automatically be added to the measured displacement to inform the surgeon on proper screw selection.

It should also be appreciated that the processor 236 may also send a command to the measurement module 128 to cause the measurement module 128 to automatically enter the Drilling Mode when the processor 236 determines that the calibration fixture 300 is no longer positioned proximate the surgical handpiece system 60. This feature could be further based on an amount of time elapsed. For example, the processor 236 may cause the measurement module 128 to reenter the Drilling Mode 15 seconds after the processor 236 determines that the calibration fixture 300 is no longer in proximity to the handpiece. It should be appreciated that while the description throughout refers to the measurement module 128 performing logical steps, those same logical steps could be performed by any component of the surgical handpiece assembly 62. These steps include, but are not limited to, performing calculations, determining proximity, and entering calibration or drilling mode.

In the system in FIGS. 8-10, the calibration housing 302 is placed over the depth measurement extension 134 and is either pressed against the distal end of the surgical handpiece system 60 or may be secured to the surgical handpiece system 60 using an interlocking mechanism (not shown).

The slider 314 of the calibration fixture 300 may be situated at the distal region of the lumen 312 of the calibration fixture 300 prior to insertion of the screw 232. The distal end of the depth measurement extension 134 abuts the proximal end 336 of the slider 314. As described above, the measurement module 128 may automatically enter the Calibration Mode when the processor 236 detects that the calibration fixture 300 is positioned proximate the surgical handpiece system 60.

When the measurement module 128 enters Calibration Mode, the depth reading is zeroed and the processor 236 waits for further input from the displacement sensor assembly 136 associated with depth measurement extension 134. The user is then prompted on the display 148 to select a screw 232 having a specific nominal screw length from the set, for example, 26 mm. A screw length between 24 and 36 mm is ideal because this length is generally included in every type of implant sets for smaller bones, such as those in the foot, as well as implant sets for larger bones, such as the femur. The bone-abutting face 238 of the plate 234 is placed against the distal end of the calibration fixture housing 302 and the screw 232 is inserted through the plate 234 into the distal end of the calibration fixture 300. The end of the screw 232 contacts the distal end 338 of the slider 314 which displaces the slider 314 and depth measurement extension 134, as shown in FIGS. 8 and 10.

In other configurations where the calibration mode has already been entered by the user input device, by the coupling of the measurement module 128 to the surgical handpiece assembly 62, or by another manner, the screw 232, plate 234, and the calibration housing 302 may engage each other before the calibration fixture 300 is place proximate the measurement module 128. The bone-abutting face 238 of the plate 234 is placed against the distal end of the calibration fixture housing 302 and the screw 232 is inserted through the plate 234 into the distal end of the calibration fixture 300. The end of the screw 232 contacts the distal end 338 of the slider 314. Then the calibration fixture 300 is placed proximate the measurement module 128 and the slider 314 displaces the depth measurement extension 134. It is contemplated that the calibration fixture 300, the measurement module 128, the screw 232, and the plate 234 may engage each other in a different order and correctly provide an accurate adjustment so long as the relative position and engagements remain the same as shown in the illustrated and described configurations herein.

In other configurations, the user may be directed to insert one of a number of screws having predetermined nominal lengths. The measurement module 128 may detect the screw 232 is of a certain nominal length based on the range in which the displacement of the depth measurement extension falls and the measurement module 128 may then determine an adjustment based on the displacement of the depth measurement extension 134 and the identified nominal screw length. For instance, the user may be prompted on the display 148 to select a screw 232 having either a first nominal screw length from the set or a second nominal screw length from the set. The measurement module 128 may automatically determine which screw was selected based on the displacement of the depth measurement extension 134 and range the displacement falls within. After the measurement module 128 determines which screw was selected the adjustment may be determined as described herein.

In some configurations, one or more adjustment parameters must be met for the measurement module 128 to register a final displacement of the depth measurement extension 134 to determine the adjustment. One adjustment parameter may be the sensor 342 determining the calibration fixture 300 is proximate the measurement module 128 to establish an accurate tolerance stack-up between the calibration fixture 300 and the measurement module 128. Another adjustment parameter may be a relative position of the depth measurement extension 134 relative the module housing 130 being within a certain range. For example, if the user selects a screw 232 from the set that is too short to displace the slider 314 and/or the depth measurement extension 134 to a certain minimum threshold, the displacement may not be registered and the user may be required to use a longer screw 232. Similarly, if the user selects a screw 232 from the set that is too long such that the slider has been displaced to maximum threshold, the displacement may not be registered and the user may be required to use a shorter screw 232. Further, if the screw 232 is too long, the head of the screw may not be abutting the plate 234 if the slider 314 is at a proximal end of the lumen 312 and the screw 232 is longer than the distance between the distal end of the slider 314 and the distal end of the calibration housing 302. Still another adjustment parameter may be that the position of the depth measurement extension 134 relative to the calibration housing 302 remain constant for a certain duration of time. For instance, the user may be required to hold the calibration housing 302 steady for a minimum amount of time, for example 0.2 to 3 seconds, in order for the measurement module 128 to register the final displacement from the selected screw.

The measurement module 128 automatically calculates and stores the length adjustment. The calculation is possible due to a mechanical stack-up of known and measured distances specified in FIG. 8. Dimension A is the length of the calibration fixture 300 from proximal 306 to distal end 310, which is also the space between the distal end of the measurement module 128 and the bone-abutting face 238 of the plate 234. Dimension B is the distance from the distal end of the measurement module 128 to the distal end of the depth measurement extension 134, which is measured using the measurement module 128. Dimension C is the length of the slider 314. Finally, Dimension D is the unknown distance from the tip of the selected screw to the bone-abutting face 238 of the plate 234.

The measurement module 128 can simply subtract Dimension B and Dimension C from Dimension A to determine Dimension D, the displacement caused by the insertion of the screw 232. Dimension D correlates to the cortex-to-cortex bone thickness, if screw 232 were inserted into bone, instead of the calibration fixture 300. Since the nominal length of screw 232 is also known, the measurement module 128 can determine the adjustment by subtracting Dimension D from the nominal screw length, and automatically saving the length adjustment for the duration of the surgical case into the memory unit. In the alternative (or in addition to), the adjustment could be reported to the user with the display 148 or speaker or both. The adjustment may be rounded. For example, because sets of screws 232 are provided in 1- or 2-mm increments, the measurement module 128, may round the outputted recommended screw length to the nearest mm or automatically round up or down to the next mm or next even mm.

Certain applications may benefit from ensuring that the screw is long enough to fully penetrate the bone, as a result in these instances rounding up may be preferable. While other operations where there is greater danger of damaging surrounding tissue with a protruding screw tip, rounding down may be preferable. The surgical handpiece system 60 may receive information regarding the planned procedure and modify its calculation of a recommended screw length accordingly.

In an exemplary calculation, based on the system shown in FIG. 8, a user may be directed to insert a screw 232 with a nominal length of 30 mm. This may yield a Dimension D of 28 mm. The adjustment is 2 mm (i.e. the difference between the 28 mm displacement, Dimension D, and the 30 mm nominal value). The 2 mm adjustment is stored. Then when drilling is completed if a cortex to cortex bone measurement is determined to be 34 mm, the measurement module 128 will output a recommended screw length of 36 mm.

Calculation by the processor instead of by hand further increases accuracy of the adjustment, as it permits additional significant figures to be included in the adjustment.

Figure 27:
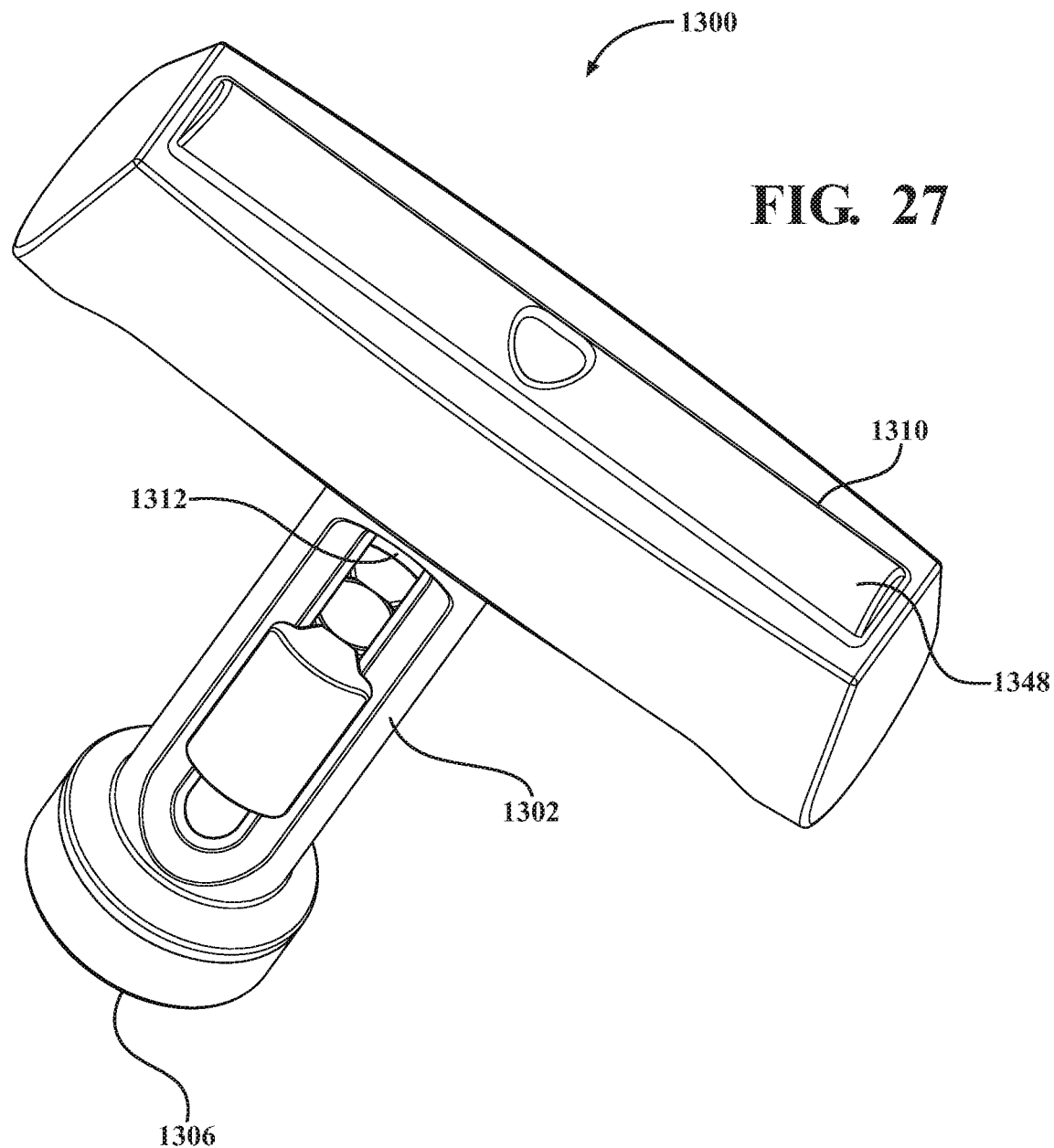
FIG. 27 is a perspective view of another calibration fixture for automatic calibration of a surgical handpiece system.
Figure 28:
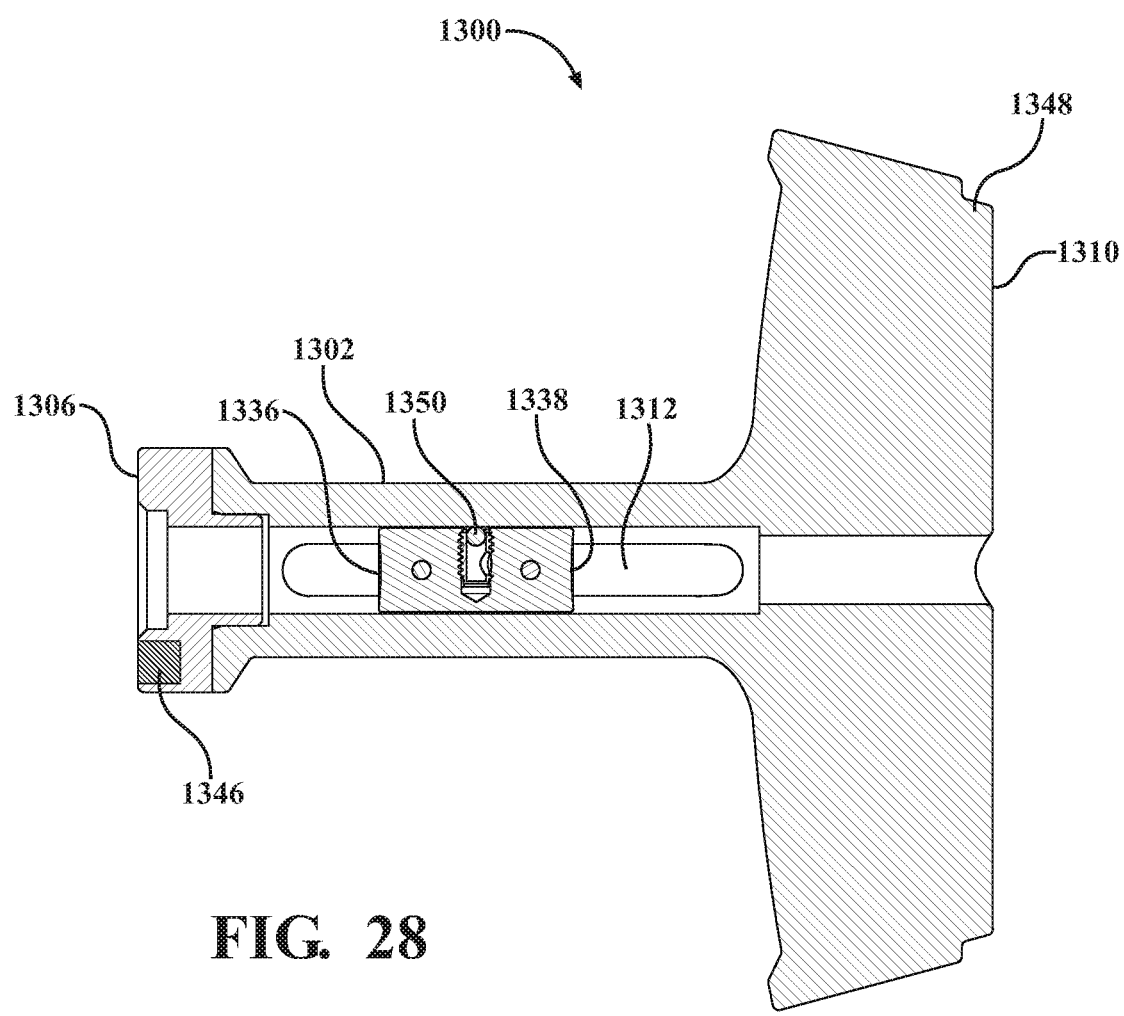
FIG. 28 is a sectional view of the calibration fixture of FIG. 27.

Referring to FIGS. 27 and 28, an alternative configuration of the calibration fixture 1300 is illustrated. It should be appreciated that the various configurations of the calibration fixture 1300 may include similar elements to those shown in FIGS. 8-10 that may be identified by reference numerals that are incremented by 1000. It should be understood that those elements including reference numerals which are incremented by 1000 can have the same features as described above.

FIGS. 27 and 28 show another calibration system that uses a surgical handpiece system 60 having the measurement module 128 interfacing with an alternative design of the calibration fixture 1300, with screw 232, and plate 234 from a set to calibrate the surgical handpiece system 60.

Similar to the calibration fixture 300 of FIGS. 8-10, the calibration fixture 1300 is shown with a T-shaped housing 1302. The T-shaped housing 1302 provides an ergonomic benefit when holding the calibration fixture 1300. The T-shape also provides more surface area for the plate 234 to rest against.

Another similarity to the calibration fixture 300 shown in FIGS. 8-10 is a calibration sensor assembly (not shown). A sensor 342 is coupled to a processor within the measurement module 128 or surgical handpiece assembly 62. The processor 236, based on the input signal from the sensor 342, is configured to determine whether the calibration fixture 1300 is positioned proximate to the surgical handpiece system 60. The sensor assembly may include a second component located in the calibration fixture 1300 and configured to emit a signal to the sensor 342. When the processor 236 determines that the calibration fixture 1300 is positioned proximate to the measurement module 128, the processor causes measurement module 128 to automatically enter the Calibration Mode. It should be appreciated that the processor may be tuned such that the processor only determines that the calibration fixture 1300 is proximate when the calibration fixture 1300 is less than a predetermined distance away from the measurement module 128, such as less than 1 mm.

In one potential implementation, the sensor 342 comprises a magneto-resistive sensor (such as a hall-effect sensor). The sensor 342 may be positioned near the distal end of the measurement module 128 or surgical handpiece assembly 62. The calibration fixture 1300 may include a magnet 1346 positioned near the proximal end 1306 of the calibration fixture 1300. It is contemplated that the sensor assembly 340 may take other suitable forms to detect the proximity of the calibration fixture 1300, for example, the sensor 342 may take the form of a mechanical button or switch that is depressed, an RFID antenna that is triggered by a coil included on the calibration fixture 1300, or a capacitive sensor.

Once the processor determines that the calibration fixture 1300 is positioned proximate to the surgical handpiece system 60 based on the sensor 342 input signal, the processor causes the measurement module 128 or surgical handpiece assembly 62 to enter calibration mode. Then—once measurement module 128 determines the length adjustment for a given plate 234 and screw 232 set through the procedure described for the system shown in FIGS. 6 and 7 and the measurement module 128 stores length adjustment in the memory unit of the measurement module 128—the user reenters the Drilling Mode. During Drilling Mode, the length adjustment may automatically be added to the measured displacement to inform the surgeon on proper screw selection.

It should also be appreciated that the processor 236 may also send a command to the measurement module 128 to cause the measurement module 128 to automatically enter the Drilling Mode when the processor 236 determines that the calibration fixture 1300 is no longer positioned proximate the surgical handpiece system 60. This feature could be further based on an amount of time elapsed. For example, the processor 236 may cause the measurement module 128 to reenter the Drilling Mode 15 seconds after the processor 236 determines that the calibration fixture 1300 is no longer in proximity to the handpiece. It should be appreciated that while the description throughout refers to the measurement module 128 performing logical steps, those same logical steps could be performed by any component of the surgical handpiece assembly 62. These steps include, but are not limited to, performing calculations, determining proximity, and entering calibration or drilling mode.

The calibration fixture housing 1302 may be placed over the depth measurement extension 134 and may be either pressed against the distal end of the surgical handpiece system 60 or may be secured to the surgical handpiece system 60 using an interlocking mechanism (not shown). The slider 1314 of the calibration fixture 1300 is situated at the distal region of the lumen 1312 of the calibration fixture 1300 prior to insertion of the screw 232. The distal end of the depth measurement extension 134 abuts the proximal end 1336 of the slider 1314. As described above, the measurement module 128 automatically may enter a calibration mode when the processor 236 detects that the calibration fixture 1300 is positioned proximate the surgical handpiece system 60. When the measurement module 128 enters Calibration Mode, the depth reading is zeroed and the processor 236 waits for further input from the displacement sensor assembly 136 associated with depth measurement extension 134. The user is then prompted on the display 148 to select a screw 232 having a specific nominal screw length from the set. The bone-abutting face 238 of the plate 234 is placed against the distal end of the calibration fixture housing 1302 and the screw 232 is inserted through the plate 234 into the distal end of the calibration fixture 1300. The end of the screw 232 contacts the distal end 1338 of the slider 1314 which displaces the slider 1314 and depth measurement extension 134.

The distal end of the calibration housing 1302 has a distal surface that may include a ridge 1348 designed to have a curvature similar to a bone and therefore closely engage a bone-abutting face 238 of the plate 234. This ridge 1348 is an optional improvement of the calibration housing 1302. Instead of a ridge, the entire distal surface of the calibration housing 1302 may be curved or flat.

The slider 1314 may include a biasing mechanism 1350 configured to abut a sidewall of the calibration housing 1302 that defines the lumen 1312 of the calibration housing 1302. The biasing mechanism prevents the slider 1314 from moving freely within the lumen 1312 of the calibration housing. It is appreciated that while free movement of the slider 1314 is restricted, the slider 1314 may still be moved via user manipulation as described above. The biasing mechanism 1350 may comprise a spring-loaded plunger. It is contemplated that other biasing mechanisms may be used to abut the sidewall of the calibration housing 1302 to prevent otherwise free movement of the slider 1314 within the lumen 1312 of the calibration housing 1302 The spring-loaded plunger may comprise a main body and a ball (or in some cases a pin) at least partially received within a recess of the main body. The ball is movably coupled to the main body to project outwardly from the main body toward a sidewall of the calibration housing 1302. A spring positioned within the recess of the main body is configured to apply a constant force against the ball to bias the ball toward the sidewall of the calibration housing 1302. Engagement of the ball against the sidewall of the calibration housing 1302 acts to prevent free movement of the slider 1314 within the lumen 1312.

Figure 11:
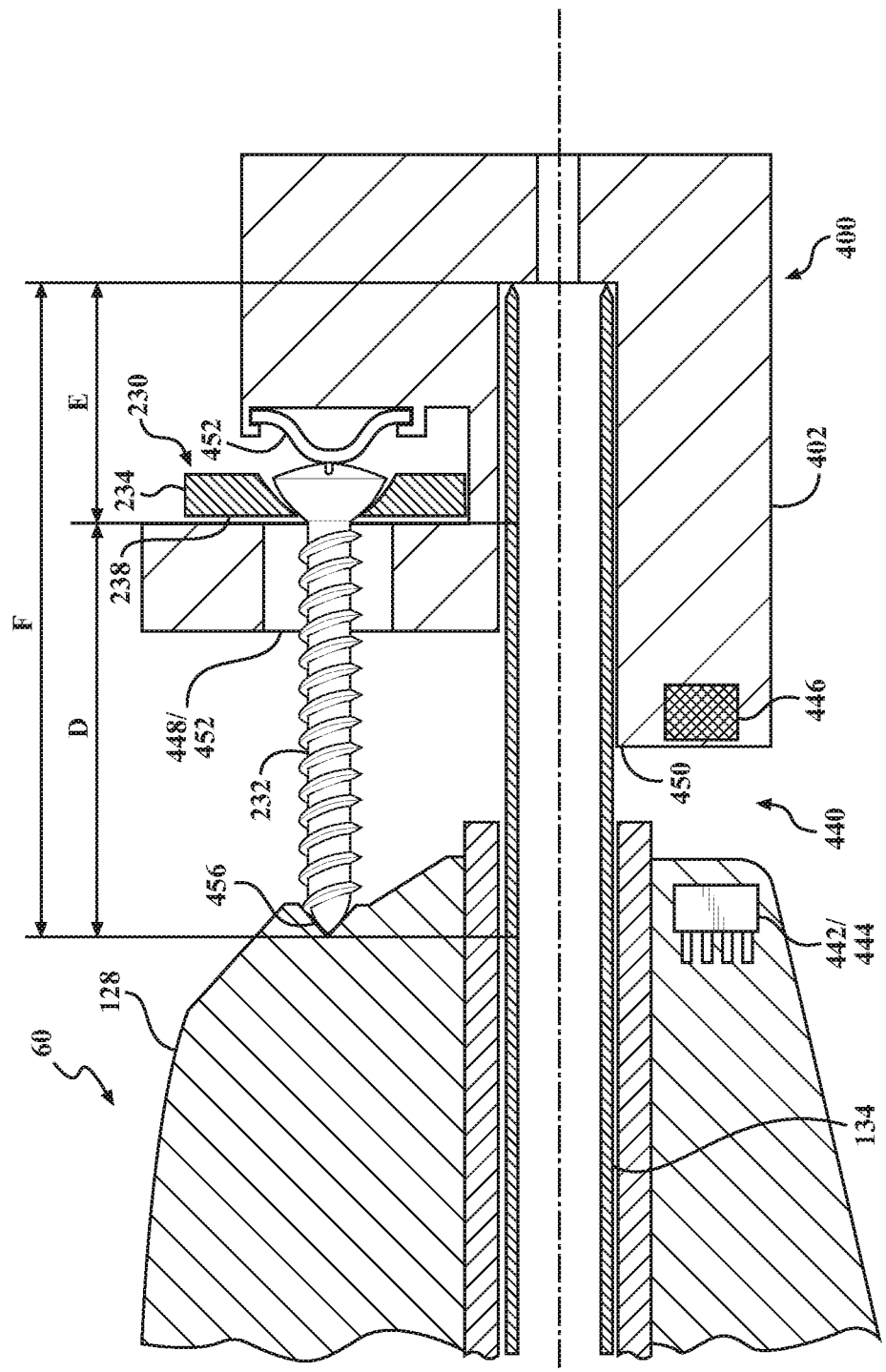
FIG. 11 is a sectional view taken longitudinally showing an alternative configuration of a calibration fixture for automatic calibration of a surgical handpiece system

An alternative housing for the above-described automated calibration is disclosed in FIG. 11. Instead of a T-shaped housing 302 (FIGS. 8-10) and T-shaped housing 1302 (FIGS. 27-28), housing 402 is used. The depth measurement extension 134, is still inserted into a first receptacle 448 in the housing 402. The screw 232 is inserted into a plate 234 and the set is inserted into a second receptacle 450 in the housing 402. The screw head is kept in place with a centering spring 452. The second receptacle 450 is open along a proximal end 406 of the calibration fixture 400 and along the side 454. Once the screw 232 is inserted through plate 234, both may be placed in the second receptacle 450 through the side opening 454 of the calibration fixture 400. Finally, a pocket 456 may be added to the distal end of the surgical handpiece assembly 62 or measurement module 128 to better secure the screw 232 tip to prevent movement during calibration.

In this configuration, the measurement module 128 may more directly calculate the Dimension D, the distance from the proximal end of the plate to the distal end of the measurement module 128, as the displacement of the depth measurement extension 134 is known and the location of the proximal end of the plate is known relative to the distal end of the depth measurement extension 134. In other words, Dimension E—the known distance from the distal end of the depth measurement extension 134 to the bone-abutting face 238 of the plate 234—may be subtracted from Dimension F—the known distance from the distal end of the depth measurement extension 134 to the pocket 456—to determine Dimension D. Again, because nominal length of the selected screw 232 is known adjustment may be determined by subtracting the Dimension D from the nominal length of the screw 232, and the adjustment may be automatically saved for the duration of the surgical case. In the alternative, the adjustment could be reported to the user.

FIGS. 14-18 depicts a system that may be used to determine the adjustment of the screw 232 and plate 234 set. This system relies on the depth gauge 260 from the set to be used (FIGS. 12 and 13) and plate 234 from the set to be used, along with a calibration block 500 to determine the adjustment. The calibration block 500 is elongated with rounded edges. The illustrated calibration block 500 was designed to fit easily within one hand, but could have several shapes, including a T shape or square corners and edges. In addition, the calibration block 500 has a top surface 502 that includes a ridge 504 designed to have a curvature similar to a bone and therefore closely engage a bone-abutting face 238 of the plate 234. This ridge 504 is an optional improvement of the calibration block 500. Instead of a ridge the entire top surface 502 of the calibration block 500 may be curved or flat. In addition, the calibration block 500 includes two holes, a smaller hole 506 and a larger hole 508. The calibration block 500 may include only one hole or more than two holes. The varying sizes of the smaller hole 506 and larger hole 508 are to provide a fit that is just larger than the depth gauge 260 provided with the screw 232 and plate 234 set. Each of the smaller hole 506 and the larger hole 508 have a known depth. In FIGS. 14 through 18, both holes 506/508 have a depth of 30 mm. Alternative designs with different depths may be used. For example, it may be useful to provide smaller holes with shorter depths to be used with depth gauges 260 provided with screw 232 and plate 234 sets for bones of the hands and feet. Larger holes may have longer depths, causing the calibration block 500 to have more of a triangular shape along its side profile. The calibration block 500 holes may also be labeled with the depth of the hole. The bottom surface 510 includes a raised edge 512 inside a depression 514 around each of the smaller and larger holes 506, 508. This raised edge 512 and the depression 514 each provide an improved surface for a hook of a depth gauge 260 to be held steady but are both also optional.

Figure 16:
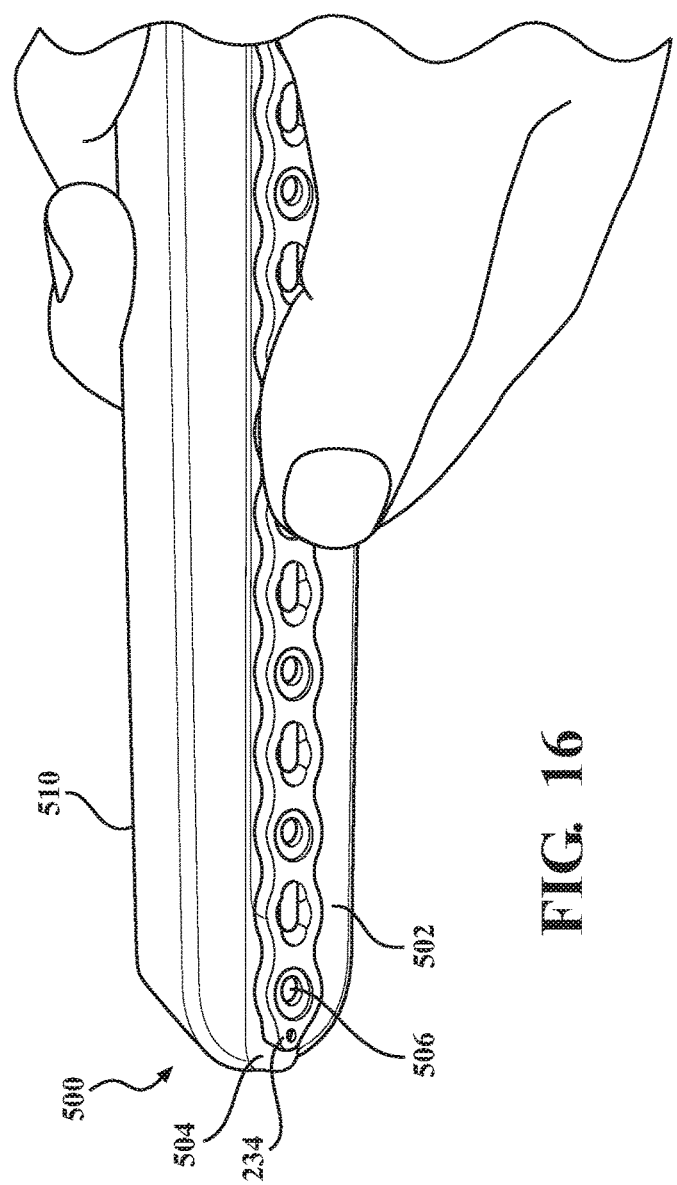
FIG. 16 is a perspective view of a surgical plate and the calibration block.
Figure 17:
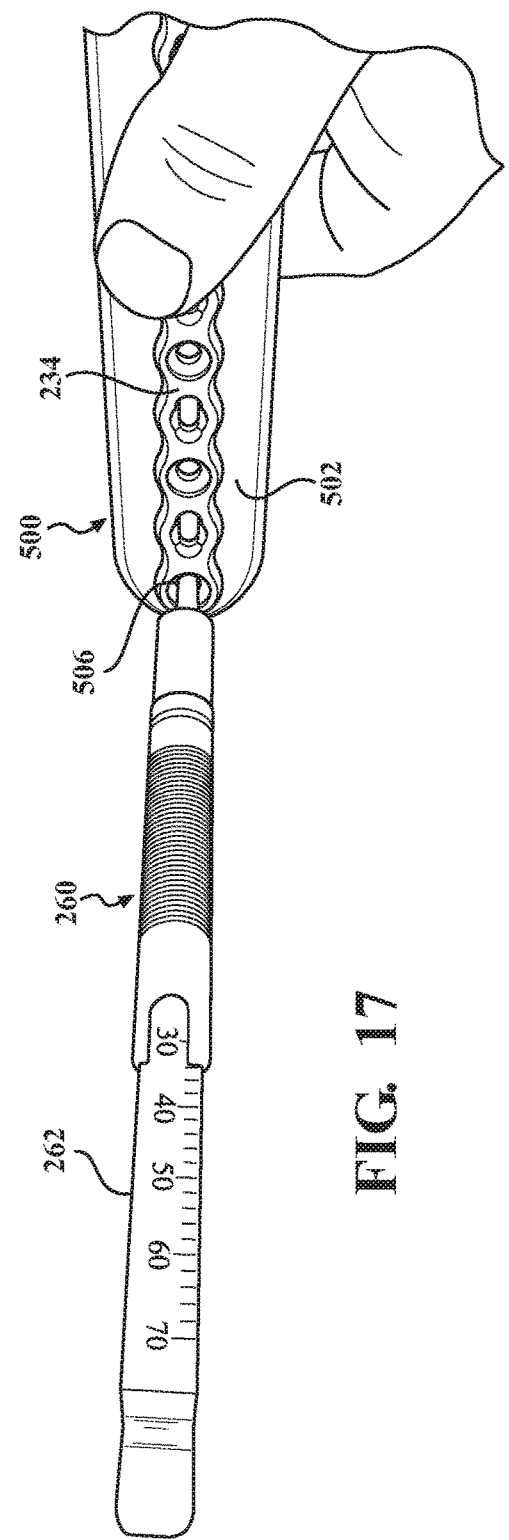
FIG. 17 is a perspective view of a depth gauge, surgical plate, and calibration block
Figure 18:
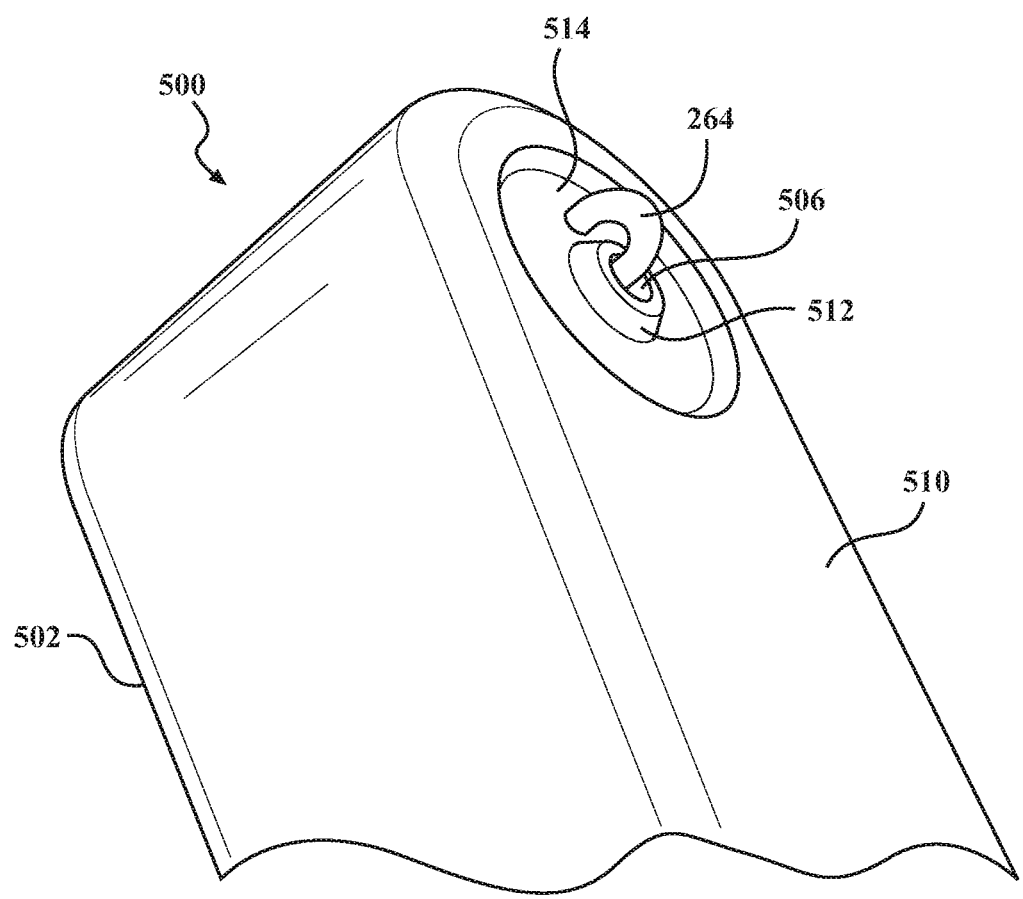
FIG. 18 is a zoomed in perspective view of the bottom surface of the calibration block and the depth gauge.

Determination of the adjustment for the orthopedic screw 232 and plate 234 set with the calibration block may be done by: Laying the plate 234 over the appropriate hole, as shown in FIGS. 16-18, the smaller hole 506 is used in this instance. The selected plate 234 should be set over the calibration block 500 in the same fashion it would be set over the bone during implantation. The bone-abutting face 238 should be placed such that it contacts top surface 502 of the calibration block 500. The depth gauge 260 is then inserted through the smaller hole 506. The hooked end 264 of the depth gauge 260 rests against the bottom surface 510 of the calibration block 500. The user than obtains a screw length from the measurement markings 262 of the depth gauge 260.

In this case, the nominal screw length is shown as 33 mm on depth gauge 260 in FIG. 17. Thus, the adjustment is 33 mm-30 mm hole depth or 3 mm. The user may retain the 3 mm adjustment and add the adjustment to the output of the measurement module 128 after drilling. Alternatively, the user may supply the adjustment to the surgical handpiece system 60 so that the outputted recommended screw length is automatically based on the nominal screw length from the manufacturer. The user may be prompted to provide the adjustment via the display 148 of the surgical handpiece system 60 prior to each case. A memory of the surgical handpiece system 60 would then store the adjustment for the duration of the surgical case.

Figure 29:
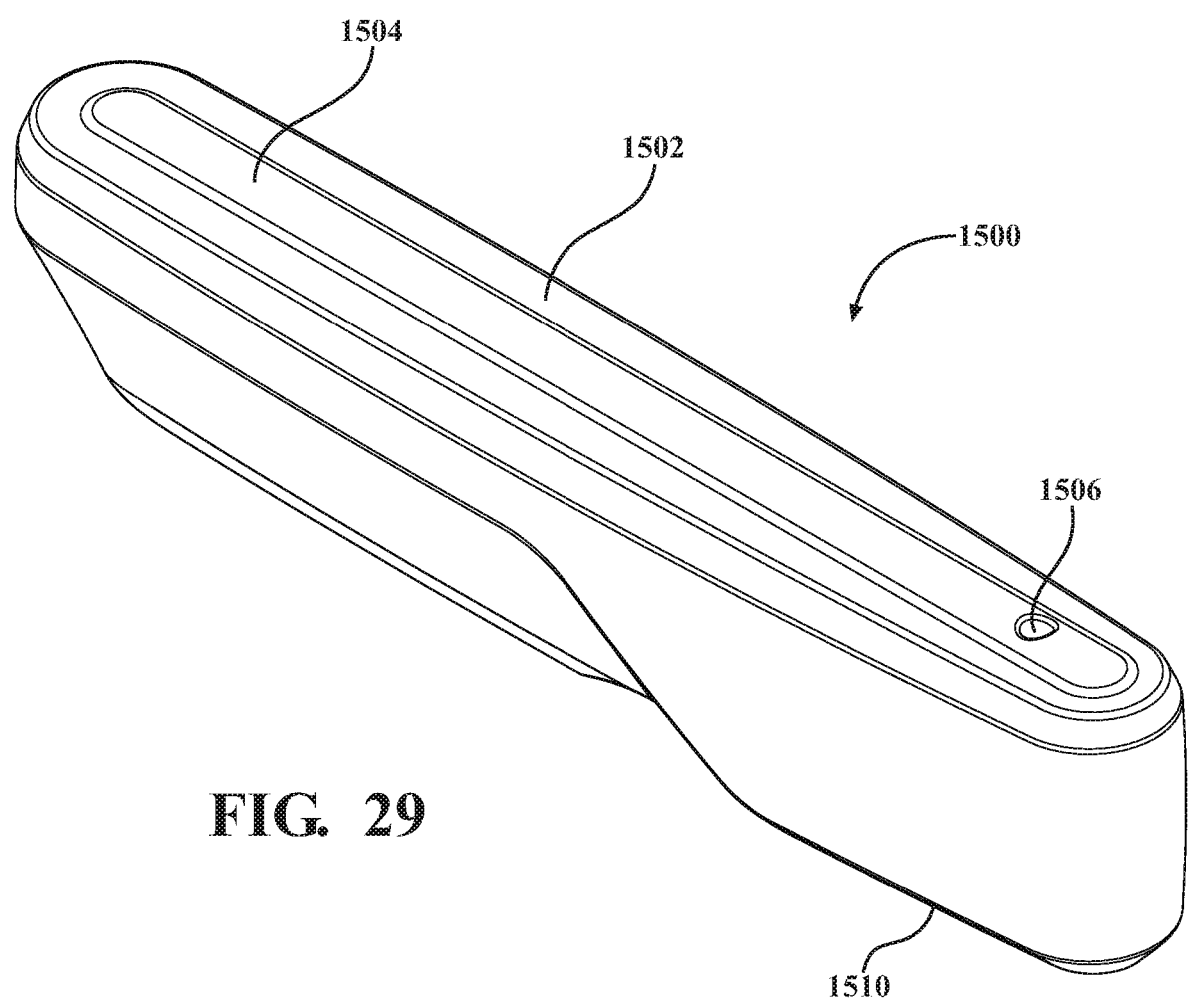
FIG. 29 is a perspective view of another calibration block.
Figure 30:
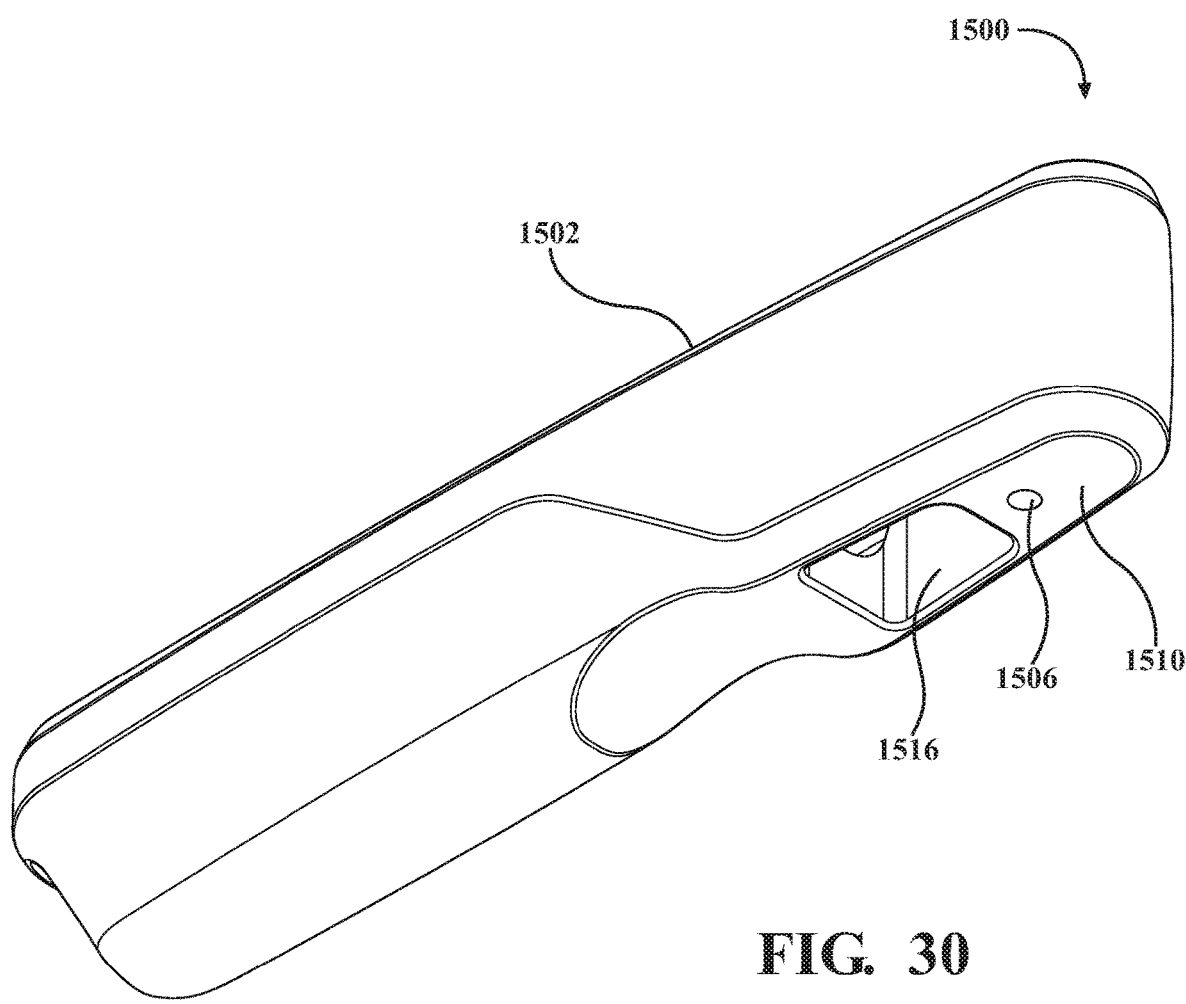
FIG. 30 is another perspective view of the calibration block of FIG. 29.
Figure 31:
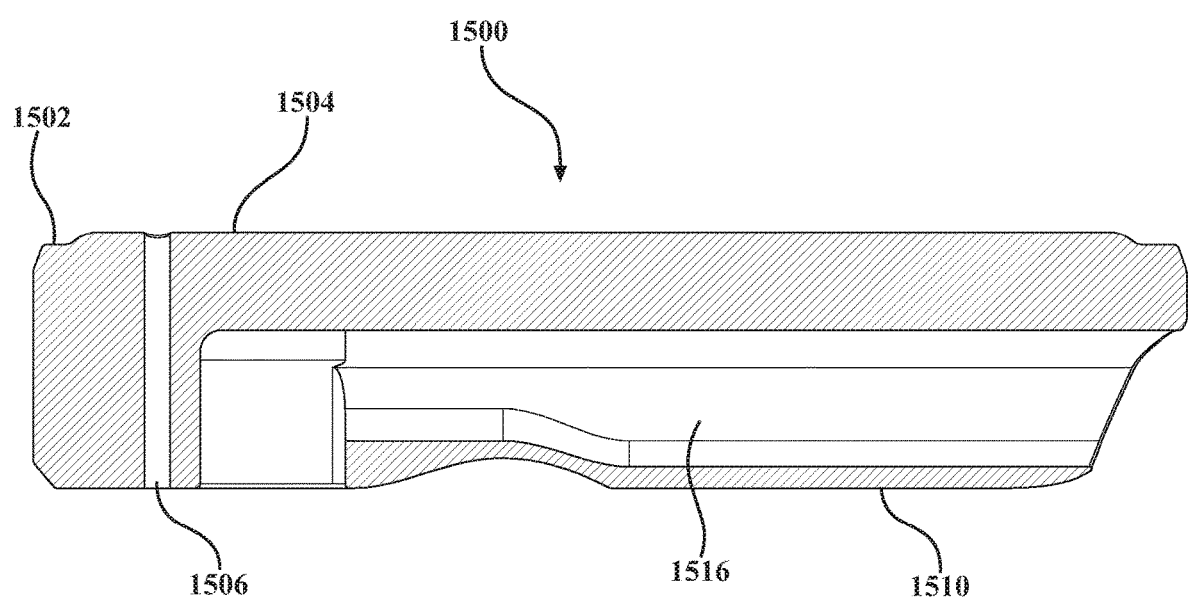
FIG. 31 is a sectional view of the calibration block of FIG. 29.

Referring to FIGS. 29-31, an alternative configuration of the calibration block 1500 is illustrated. It should be appreciated that the various configurations of the calibration block 1500 may include similar elements to those shown in FIGS. 14-18 that may be identified by reference numerals that are incremented by 1000. It should be understood that those elements including reference numerals which are incremented by 1000 can have the same features as described above.

FIGS. 29-31 depicts a system that may be used to determine the adjustment of the screw 232 and plate 234 set. This system relies on the depth gauge 260 from the set to be used (FIGS. 12 and 13) and plate 234 from the set to be used, along with a calibration block 1500 to determine the adjustment. The calibration block 1500 is elongated with rounded edges. The illustrated calibration block 1500 was designed to fit easily within one hand, but could have several shapes, including a T shape or square corners and edges. Further, the calibration block 1500 comprises contoured sides to assist the user in grasping the calibration block 1500. In addition, the calibration block 1500 has a top surface 1502 that includes a ridge 1504 designed to have a curvature similar to a bone and therefore closely engages a bone-abutting face 238 of the plate 234. This ridge 1504 is an optional improvement of the calibration block 1500. Instead of a ridge, the entire top surface 1502 of the calibration block 1500 may be curved or flat. In addition, the calibration block 1500 includes a hole 1506. The calibration block 1500 may include more than one hole. The hole 1506 has a known depth.

Determination of the adjustment for the orthopedic screw 232 and plate 234 set with the calibration block 1500 may be done by: Laying the plate 234 over the hole 1506. The selected plate 234 should be set over the calibration block 1500 in the same fashion it would be set over the bone during implantation. The bone-abutting face 238 should be placed such that it contacts top surface 1502 of the calibration block 1500. The depth gauge 260 is then inserted through the hole 1506. The hooked end 264 of the depth gauge 260 rests against a bottom surface 1510 of the calibration block 1500. The user than obtains a screw length from the measurement markings 262 of the depth gauge 260.

The calibration block 1500 may define a cavity 1516 to reduce the weight of the calibration block 1500. The cavity 1516 being open at two ends advantageously allows for easier cleaning of the cavity. However, it is contemplated that the cavity 1516 may instead be closed at one end such that the cavity creates a blind hole.

During certain surgical procedures it may be desirable to insert a screw 232 or other implant at an oblique angle into a patient's bone. In such a procedure, a suitable selection of a screw length for the procedure may require the nominal screw length to be further compensated. In some procedures, a head of the screw 232 may not seat fully into the bevel on the proximal side of the bone plate 234 or fully parallel to the outer surface of a proximal cortex 550 (see FIGS. 21A-24) of the patient's bone when inserted at an oblique angle. For example, during a procedure requiring drilling through proximal and distal cortex, when the screw is inserted at an oblique angle, the head of the screw 232 may abut a different portion of the plate 234 than what the head of the screw would abut if the screw was orthogonal to the hole of the plate, which may prevent the screw 232 from being fully seated in the plate hole. If the head of the screw 232 is not fully seated into the plate hole and no compensation took place, the selected screw length output by the measurement head may be shorter than desired and during the procedure, the screw 232 may not be inserted through or to the distal cortex 552. By adding a compensation length based on the angle at which the screw 232 is inserted, the possibility that a screw 232 will be too short is mitigated. This compensation length may be in addition to the adjustment length provided from calibration of the surgical handpiece system 60 for various combinations of plates 234 and screws 232 as described above. In other words, the suitable screw length may be selected by calibrating the surgical handpiece system 60 for the specific screw 232 type and plate 234 selected and by compensating the calibrated screw length value for the angle at which the screw 232 is inserted. It is contemplated that in some configurations where calibration is not necessary or when calibration is not otherwise performed for the specific screw type or plate, that the nominal screw length may still be compensated for the angle at which the screw 232 is inserted.

Referring to FIG. 4, the surgical handpiece assembly 62 comprises a sensor 554 configured to generate an orientation signal responsive to orientation of the surgical handpiece assembly 62 and more specifically the orientation of the depth measurement extension 134 and the measurement axis MX the depth measurement extension 134 extends along. The controller 78 is configured to receive the signal from the sensor 554 and determine the suitable screw length for bone fixation based on the signal from the sensor 554. The sensor 554 may be an accelerometer, a gyroscopic sensor, a stereoscopic sensor, or another sensor configured to generate signals to the controller 78 responsive to the orientation of the surgical handpiece assembly 62. The sensor 554 may be coupled to the module housing 130 to be releasably attached to the handpiece housing assembly 74. Alternatively, the sensor 554 may be coupled to the handpiece housing assembly 74 in configurations where the module housing 130 is integral with the handpiece housing assembly 74.

Figure 19:
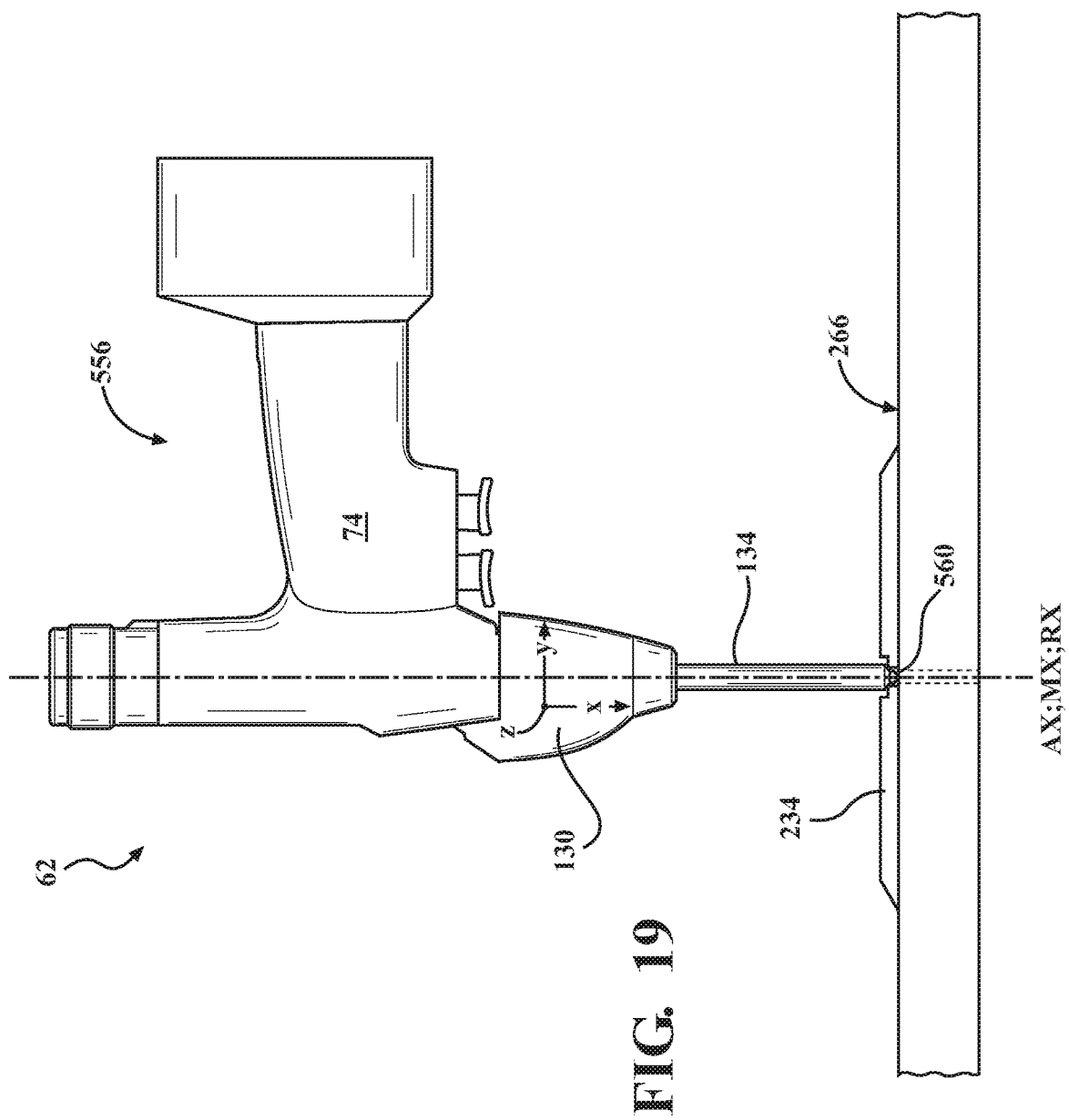
FIG. 19 is an elevation view of a surgical handpiece assembly having a depth measurement extension in a first orientation.
Figure 20:
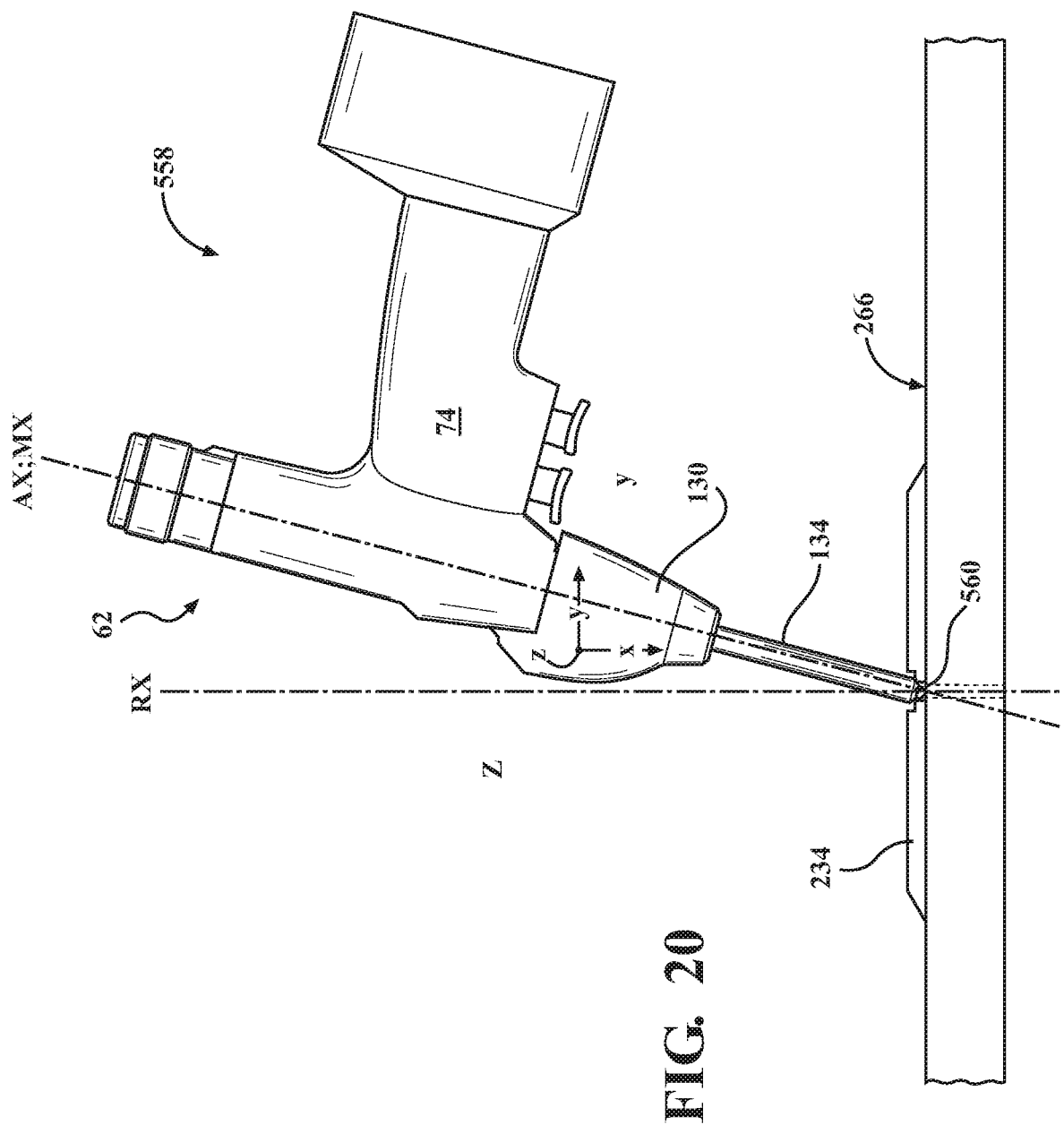
FIG. 20 is an elevation view of the surgical handpiece assembly having the depth measurement extension in a second orientation.

Referring to FIGS. 19 and 20, the angle at which the surgical handpiece assembly 62 drills the hole may be used to determine the angle that the screw 232 is to be inserted to find the compensation length. The depth measurement extension 134 may be movable by a user between a reference orientation 556 (shown in FIG. 19) and a drilling orientation 558 (shown in FIG. 20). In the reference orientation 556, the measurement axis MX is aligned with a reference axis RX extending through a hole 560 defined by the bone plate 234. In many configurations, the reference axis RX is perpendicular to one or both the bone 266 and the bone plate 234. In the drilling orientation 558, the measurement axis MX of the depth measurement extension 134 is at an oblique angle relative to the reference axis RX. This oblique angle is the drilling angle that the screw 232 will later be inserted at.

The controller 78 may be configured to receive the orientation signal from the sensor 554 corresponding to the depth measurement extension 134 being in the drilling orientation 558. The controller 78 may then be configured to determine the drilling angle of the depth measurement extension 134 based on the orientation signal. Then, the controller 78 may be configured to determine a compensation length based on the drilling angle. The controller 78 may then use the compensation length to compensate either a nominal screw length or a calibrated screw length responsive to the drilling angle to determine a suitable screw length for bone fixation.

As shown in FIG. 4, in configurations where the sensor 554 comprises a gyroscopic sensor 554, the gyroscopic sensor 554 may be coupled to the module housing 130. In other configurations, the gyroscopic sensor 554 is coupled to the handpiece housing assembly 74. The gyroscopic sensor 554 may generate the orientation signal responsive to angular velocity. The orientation signal may comprise angular velocity values in at least two of X, Y, and Z directions (see FIGS. 19 and 20) that correspond to a change in orientation of the depth measurement extension 134 as the depth measurement extension 134 moves from the reference orientation 556 to the drilling orientation 558. The controller 78 may be configured to determine the drilling angle of the depth measurement extension 134 by integrating the angular velocity values over a duration of time. The duration of time may begin when the reference orientation 556 is established and the duration of time may end when the drilling orientation 558 is established. By integrating the angular velocity values, the controller 78 may then determine the change in orientation of the depth measurement extension 134 from the reference orientation 556 to the drilling orientation 558, and thus the controller 78 may determine the drilling angle between the reference and the drilling orientations 556, 558.

The user may operatively engage a user input of the surgical handpiece system 60 to establish the reference orientation 556 and the drilling orientation 558. Alternatively, the controller 78 may be configured to generate signals responsive to certain parameters to establish the reference and drilling orientations 556, 558. Some of these parameters are discussed below. Establishing the reference and drilling orientations 556, 558 may promote controller 78 accuracy in determining the drilling angle based on the user's deliberate orientation/manipulation of the surgical handpiece assembly 62 relative to the bone plate 234. Said differently, the possibility that the controller 78 determines a false drilling angle from the orientation signal generated from the sensor 554 is mitigated when the user operatively engages the surgical handpiece assembly 62 to establish the reference and the drilling orientations 556, 558 or when certain parameters are met to establish the reference and drilling orientations 556, 558.

As stated above, the displacement sensor assembly 136 may be configured to generate a displacement signal to the controller 78 responsive to displacement of the drill bit 66 relative to the depth measurement extension 134 during or leading up to the drilling process. One or both the reference and drilling orientations 556, 558 may be established by the controller 78 (i) receiving the displacement signal, and (ii) determining the drill bit 66 has been displaced relative to the depth measurement extension 134 by a predetermined distance.

Figure 21A:
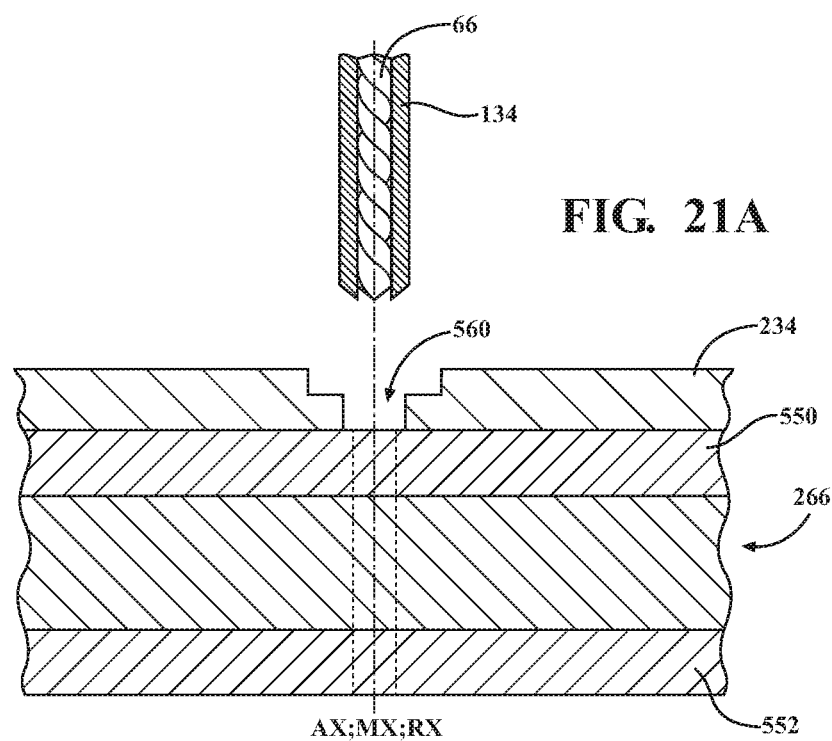
FIG. 21A is a sectional view of a drill bit and the depth measurement extension of the surgical handpiece assembly approaching a proximal cortex of a bone.
Figure 21B:
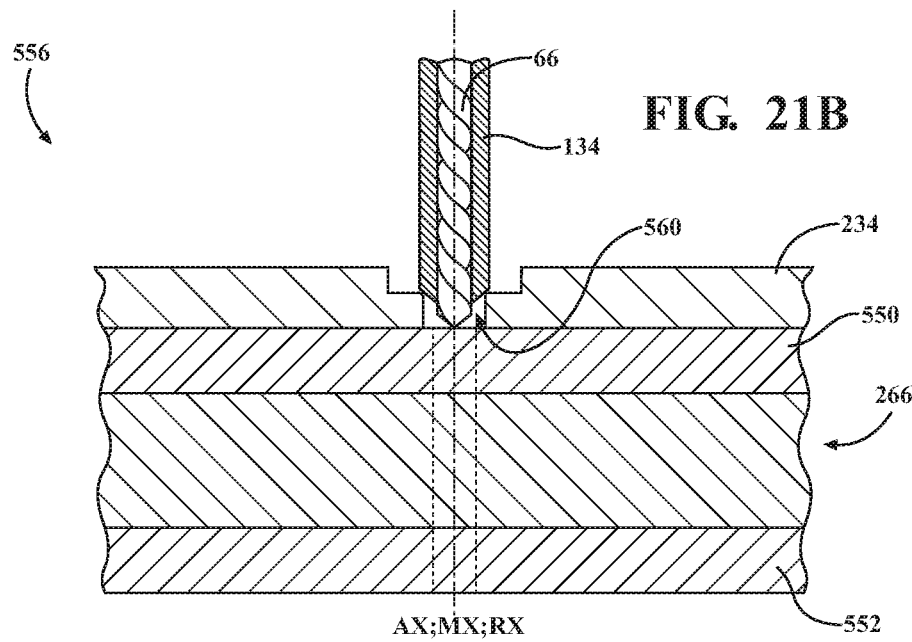
FIG. 21B is a sectional view of the drill bit and the depth measurement extension of the surgical handpiece assembly against the proximal cortex of the bone.

Referring to FIGS. 21A-24, one configuration of the surgical handpiece assembly 62 is shown before and during the drilling process. Although FIGS. 21A-24 illustrate a bone plate 234 being disposed on the outer surface of the proximal cortex 550 of the bone 266, it is contemplated that the drilling angle may also be determined when a bone plate 234 is absent. In FIG. 21A, the surgical handpiece assembly 62 is spaced from the bone plate 234 and the depth measurement extension 134 is not yet in the reference orientation 556. In FIG. 21B (corresponds to FIG. 19), the depth measurement extension 134 is shown in the reference orientation 556. As the depth measurement extension 134 is moved from its position shown in FIG. 21A to its position shown in FIG. 21B, the depth measurement extension 134 is displaced relative to the drill bit 66. The controller 78 may be configured to receive a displacement signal responsive to displacement of the depth measurement extension 134 relative to the drill bit 66 and determine the depth measurement extension 134 is in the reference orientation 556. Establishing the reference orientation 556 may provide a "zero offset" or baseline from which the drilling angle is determined. For instance, in the configuration including a gyroscopic sensor 554, the gyroscopic sensor 554 may begin generating signals corresponding to angular velocity in at least two of X, Y, and Z directions (see FIGS. 19 and 20) when the reference orientation 556 is established.

Figure 22:
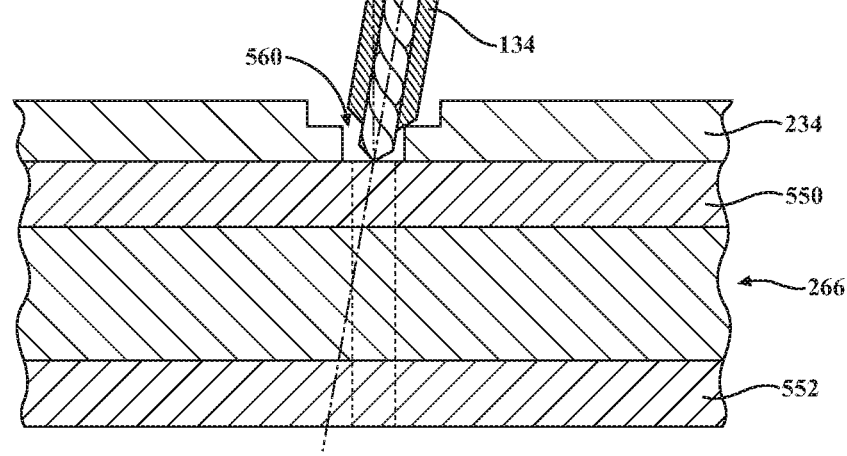
FIG. 22 is a sectional view of the drill bit and the depth measurement extension of the surgical handpiece assembly against the proximal cortex of the bone at an oblique angle to the bone.
Figure 23:
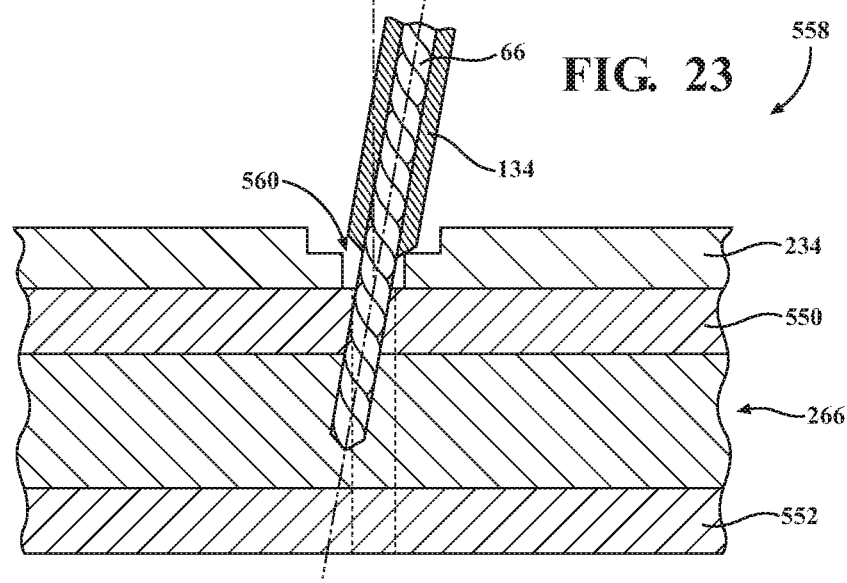
FIG. 23 is a sectional view of the drill bit and the depth measurement extension of the surgical handpiece assembly with the drill bit through the proximal cortex of the bone at an oblique angle to the bone.
Figure 24:
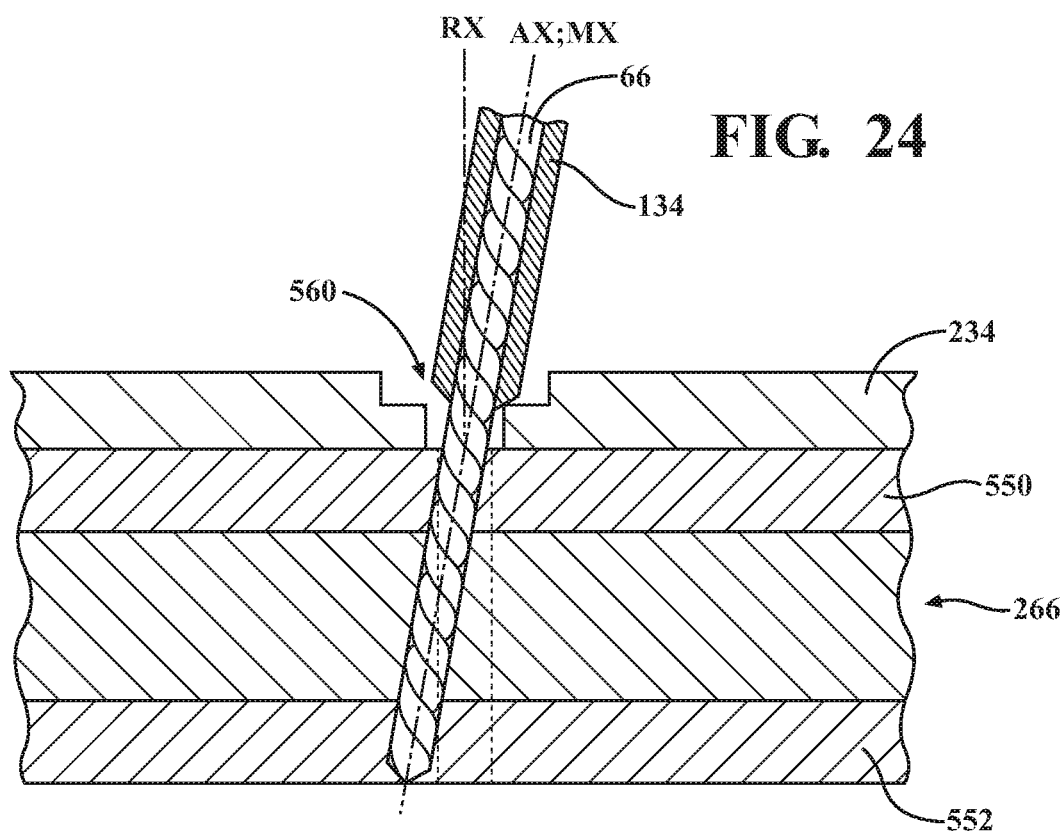
FIG. 24 is a sectional view of the drill bit and the depth measurement extension of the surgical handpiece assembly with the drill bit through the proximal cortex and a distal cortex of the bone at an oblique angle to the bone.

In FIG. 22, the surgical handpiece assembly 62 is in line with the drilling angle (corresponding to FIG. 20), however, the drilling orientation 558 of the depth measurement extension 134 may not yet have been established. In FIG. 23, the depth measurement extension 134 is shown in the drilling orientation 558. As the depth measurement extension 134 is moved from its position shown in FIG. 22 to its position shown in FIG. 23, the depth measurement extension 134 is displaced relative to the drill bit 66. The controller 78 may be configured to receive a displacement signal responsive to displacement of the depth measurement extension 134 relative to the drill bit 66 and determine the depth measurement extension 134 is in the drilling orientation 558. Although FIG. 23 shows the drill bit 66 has been displaced through the proximal cortex 550 in the drilling orientation 558, it is contemplated that the drill bit 66 may not need to enter to such a depth in the bone 266 for the controller 78 to determine the depth measurement extension 134 is in the drilling orientation 558. Instead, the controller 78 may determine the depth measurement extension 134 is in the drilling orientation 558 when the displacement of the depth measurement extension 134 relative the drill bit 66 has exceeded a predetermined displacement (e.g., 5 mm in bone 266). In the configuration including the gyroscopic sensor 554, the gyroscopic sensor 554 may cease generating signals corresponding to angular velocity when the drilling orientation 558 is established. As stated above, the controller 78 may then integrate the angular velocity values over the duration of time between when the reference orientation 556 was established and when the drilling orientation 558 was established.

In another configuration, one or both the reference and the drilling orientations 556, 558 may be established by motor state signals. The surgical handpiece assembly 62 may comprise another sensor 562 (see FIG. 4) configured to generate a motor state signal to the controller 78 responsive to a state of the motor 84. One or both the reference and drilling orientations 556, 558 may be established by the controller 78 determining that the state of the motor 84 has changed from an idle state to a running state. In one configuration, the motor state signal corresponds to a torque generated by the motor 84. The motor 84 does not generate torque in the idle state and the motor 84 generates torque in the running state. In another configuration, the motor state signal corresponds to a rotational speed of the motor 84. The motor 84 operates at a rotational speed below a rotational speed threshold in the idle state and the motor 84 operates at another rotational speed above the rotational speed threshold in the running state. In one configuration, the sensor 562 may be an accelerometer disposed in the measurement module 128. Alternatively, a single sensor may be used to determine both the angular offset and the motor state.

In one exemplary configuration, the user may be orienting the depth measurement extension 134 to the drilling orientation 558 from the reference orientation 556. The drilling orientation 558 may be established when the controller 78 determines from the motor state signal that the motor 84 has changed from the idle state to the running state.

In another configuration, one or both the reference and the drilling orientations 556, 558 may be established by actuation of the trigger 80 (user input device 80 above). The trigger 80 may be used to generate a trigger signal responsive to actuation of the trigger 80 by the user to the controller 78 for operating the motor 84 to generate torque. One or both the reference and drilling orientations 556, 558 may be established by the controller 78 determining that the trigger 80 has been actuated. In one exemplary configuration, the user may be orienting the depth measurement extension 134 to the drilling orientation 558 from the reference orientation 556. The drilling orientation 558 may be established when the controller 78 determines from the trigger signal that the trigger 80 has been actuated.

In still another configuration, one or both the reference and drilling orientations 556, 558 may be established by a user input device 564. The surgical handpiece assembly 62 may comprise the user input device 564 separate from the user input device 80 (trigger) used to operate the motor 84 above. The user input device 564 may be coupled to a measurement head, such as module housing 130 as illustrated in FIG. 1. Alternatively, the user input device 564 may instead be coupled to the handpiece housing assembly 74. The user input device 564 may be operable to generate a first reference signal to the controller 78 to establish that the measurement axis MX is aligned with the reference axis RX and to establish the depth measurement extension 134 is in the reference orientation 556. For example, the user may orient the depth measurement extension 134 to the reference orientation 556 and then actuate (e.g., press a button) the user input device 564 to generate the first reference signal to the controller 78. The controller 78 may then determine the depth measurement extension 134 is in the reference orientation 556. Likewise, the same or another user input device may be actuated a second time to generate the same or a second reference signal to the controller 78 to establish the drilling orientation 558.

In another configuration, one or both the reference and the drilling orientations 556, 558 may be established by the controller 78 determining the orientation signal from the sensor 554 of the depth measurement extension 134 have remained generally constant for a predetermined duration of time such that the depth measurement extension 134 has remained static. In one exemplary configuration, the user may be orienting the depth measurement extension 134 to the drilling orientation 558 from the reference orientation 556. The drilling orientation 558 may be established when the controller 78 determines from the orientation signal that the depth measurement extension 134 has remained static for more than a predetermined duration of time. The predetermined duration of time may vary, but exemplary times are for at least 3, 5 or 10 seconds.

It is contemplated that one or both the reference and drilling orientations 556, 558 may be established in a different manner than specified above. It is also contemplated that one or both the reference and drilling orientations 556, 558 may be established using a combination of the configurations described above. For example, in FIG. 21A, the surgical handpiece assembly 62 is spaced from the bone plate 234 and the depth measurement extension 134 is not yet in the reference orientation 556. After the user manipulates the surgical handpiece assembly 62 so that the depth measurement extension 134 is in the reference orientation 556 shown in FIG. 21B (corresponds to FIG. 19), the user may actuate the user input device 564 to generate a reference signal to the controller 78 and the controller 78 may determine that the reference orientation 556 is established. The user may then manipulate the depth measurement extension 134 to the orientation shown in FIG. 22 (corresponds to FIG. 19) and begin drilling through the proximal cortex 550. After the drill bit 66 has exceeded a predetermined displacement relative to the depth measurement extension 134, the controller 78 may determine that the drilling orientation 558 has been established.

After the controller 78 determines the drilling angle, the controller 78 may determine the compensation length by using a function that is at least partially dependent on the drilling angle. The function may also be dependent on the nominal screw length or the calibrated screw length including the adjustment length. Alternatively, the controller 78 may determine the compensation length by using a look-up table that is at least partially dependent on the drilling angle. More specifically, the look-up table may associate particular ranges of drilling angles with a single compensation length. In one exemplary configuration, a drilling angle between 0

(zero) degrees and 10 (ten) degrees may output a compensation length of 0 mm (zero mm); a drilling angle greater than or equal to 10 (ten) degrees and less than 45 (forty-five) degrees may output a compensation length of 1 mm (one mm); and a drilling angle greater than or equal to 45 (forty-five) degrees may output a compensation length of 2 mm (two mm). Other ranges for drilling angles and associated compensation lengths are contemplated. Alternatively, the controller 78 may determine the compensation length by interpolating between discrete angles using a look-up table. More specifically, the look-up table may associate discrete drilling angle values with compensation lengths such that each drilling angle value listed in the look-up table corresponds to a single compensation length and if an observed drilling angle is between two drilling angle values in the look-up table, the controller 78 may determine the compensation length by interpolating between the compensation lengths corresponding to the two drilling angle values. For instance, the look-up table may provide a compensation length of 1 mm for a drilling angle of 10 (ten) degrees and a compensation length of 1.5 mm for a drilling angle of 30 (thirty) degrees. When the drilling angle is at 20 (twenty) degrees, the controller 78 may determine that compensation length is 1.25 mm. It is contemplated that interpolation may be accomplished using a linear relationship as described in the example or another function dependent on drilling angle. The look-up table may also be dependent on the nominal screw length or the calibrated screw length including the adjustment length. The look-up table and other computer software described herein may be stored on memory in the measurement module 128 or in memory associated with a remote device, such as a tablet, that is in wireless communication with the measurement head.

After the compensation length is determined, the controller 78 may be configured to output a suitable screw length for bone fixation that is dependent upon the nominal screw length (determined from displacement of the depth measurement extension 134 after drilling) and one or both of the compensation length (determined from the drilling angle) and the adjustment length (determined during calibration for the specific plate 234 and screw 232 type selected).

Figure 25:
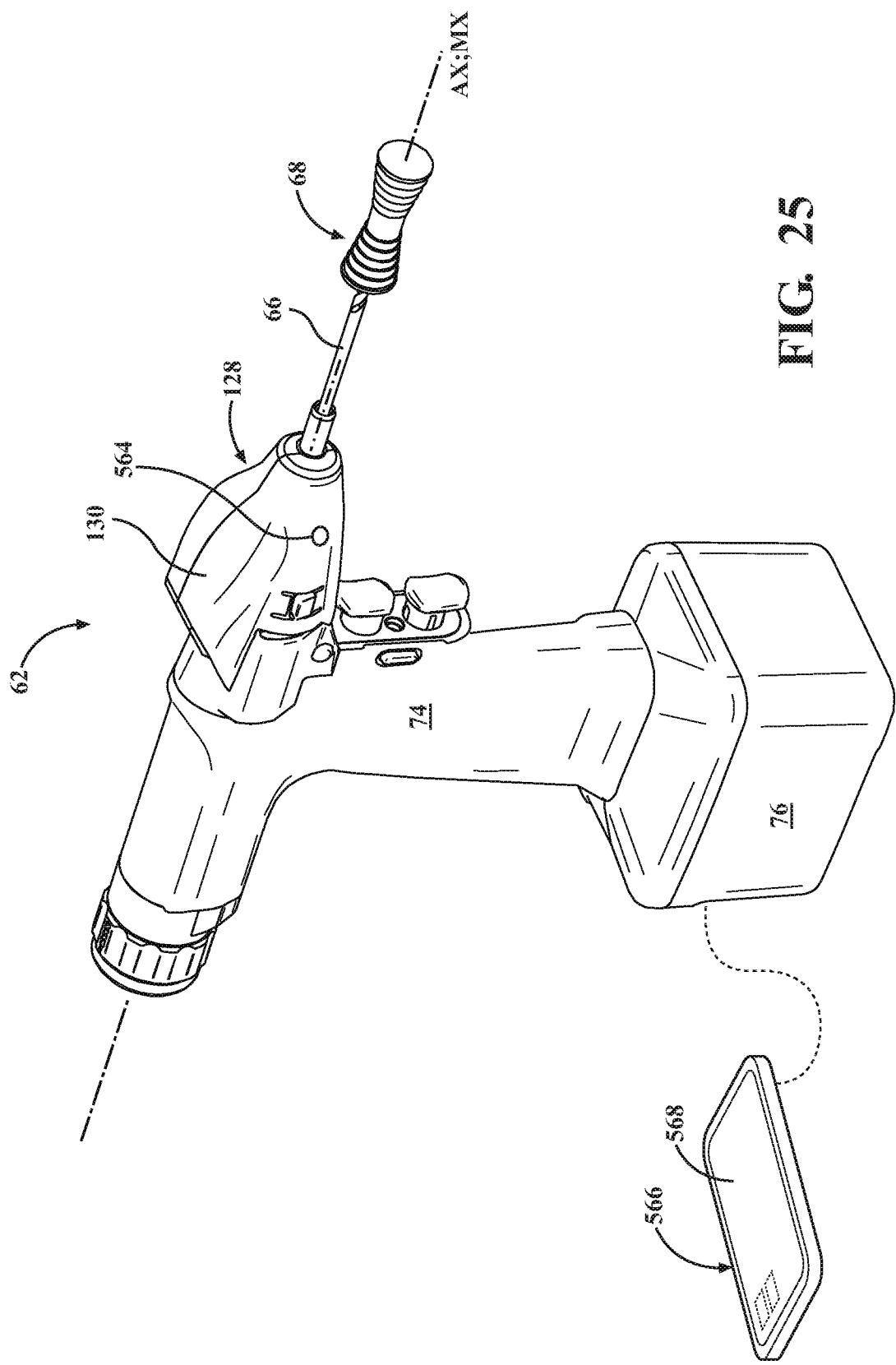
FIG. 25 is a perspective view of the surgical handpiece system including the surgical handpiece assembly and a remote device.
Figure 26:
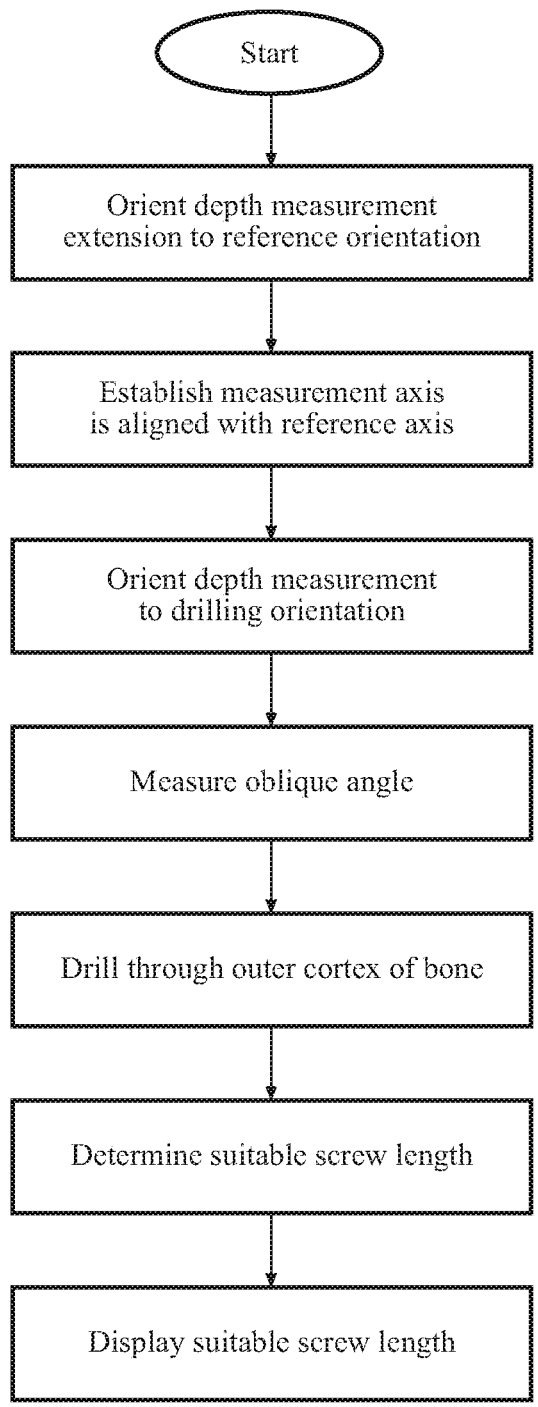
FIG. 26 is an exemplary flowchart performed by the surgical handpiece system according to the teachings of the present disclosure.

Referring to FIG. 25, the surgical handpiece system 60 may comprise a remote device 566 having a display 568. The remote device 566 may be configured to generate signals to and receive signals from the surgical handpiece assembly 62. The remote device 566 in FIG. 25 comprises a tablet. However, it is contemplated that the remote device 566 could instead comprise a smart-phone, a laptop, a workstation, or a desktop computer. One or both the display 148 on surgical handpiece assembly 62 and the display 568 on the remote device 566 may output one or more of the suitable screw length, the compensation length, the adjustment length, the nominal screw length, the displacement of the depth measurement extension 134, the drilling angle, the specific plate 234 used, the specific screw 232 type used, and other information associated with the surgical handpiece system 60.

In one configuration, one or both the surgical handpiece assembly 62 and the remote device 566 comprise a user input device (not shown) for entering or selecting information to the controller 78. The user may enter or select an oblique drilling factor in place of the compensation length for compensating the nominal screw length or the calibrated screw length including the adjustment length. The controller 78 may be configured to determine a suitable screw length based on the nominal screw length (determined from displacement of the depth measurement extension 134 after drilling), the adjustment length (determined during calibration for the specific plate 234 and screw 232 type selected), and the oblique drilling factor entered/selected by the user. The suitable screw length may be output to one or both the display 148 on surgical handpiece assembly 62 and the display 568 on the remote device 566.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency. In this application, including the definitions below, the term "controller" may be replaced with the term "circuit." The term "controller" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various implementations the controller may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 1076-2008 (commonly called "VHDL"). The hardware description language may be used to manufacture and/or program a hardware circuit. In some implementations, some or all features of a controller may be defined by a language, such as IEEE 1666-2005 (commonly called "SystemC"), that encompasses both codes, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple controllers. The term group processor circuit encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit encompasses a memory circuit that, in combination with additional memories, stores some or all code from one or more controllers.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject matter of a claim dependent from one independent claim can also be implemented in connection with another independent claim.

The present disclosure also comprises the following clauses, with specific features laid out in dependent clauses, that may specifically be implemented as described in greater detail with reference to the configurations and drawings above.

I. A system for calibrating a surgical handpiece system capable of determining drill depth to an orthopedic implant set, said system comprising:
   said surgical handpiece system comprising a depth measurement extension and configured to determine a thickness of bone when a drill bit is attached and used to drill through the bone; and
   a calibration fixture configured to engage with said depth measurement extension of said surgical handpiece system to determine an adjustment of the orthopedic implant set, said calibration fixture comprising:
      a housing defining a receptacle configured to receive a surgical screw of the orthopedic implant set, said housing having a first end configured to approach a distal surface of said surgical handpiece system to axially fix the housing of said calibration fixture relative to said surgical handpiece system; and
      a slider movably coupled to said housing and configured to move axially relative to said housing, wherein said slider has a proximal surface configured to engage with said depth measurement extension of said surgical handpiece system and a second surface configured to engage with the surgical screw, wherein the adjustment is determined based on the displacement of said depth measurement extension.

II. The system of clause I, wherein said surgical handpiece system is releasably coupled to said calibration fixture.

III. The system of any of clauses I-II, wherein the surgical handpiece system further comprises a measurement module removably coupled to a body of said surgical handpiece system, said measurement module including said depth measurement extension.

IV. The system of clause III, wherein said measurement module includes a display.

V. The system of any of clauses wherein said measurement module comprises a memory to store the adjustment.

VI. The system of any of clauses III-V, wherein said measurement module is configured to output a nominal screw length based on the adjustment.

VII. The system of any of clauses I-VI, wherein an opening to the receptacle is on the distal surface of the housing and is configured to receive the surgical screw through a surgical plate of the orthopedic implant set intended for use in surgery.

VIII. The system of any of clauses I-VII, wherein said calibration fixture is cylindrical.

IX. The system of any of clauses I-VIII, wherein said calibration fixture is T shaped.

X. The system of clause IV, wherein said measurement module comprises a processor.

XI. The system of clause X, wherein said surgical handpiece system is configured to operate in multiple modes, including a drilling mode and a calibration mode.

XII. The system of any of clauses X-XI, wherein said processor is configured to receive a nominal size of the surgical screw from the user and subtract a displacement value of the depth measurement extension to determine the adjustment.

XIII The system of any of clauses X-XII, wherein the display is configured to provide the displacement value to the user and the measurement module includes a user interface configured to receive the adjustment from the user.

XIV. The system of any of clauses I-XIII, wherein said surgical handpiece system comprises a sensor assembly configured to detect the presence of said calibration fixture in a calibration position relative to said surgical handpiece system.

XV. The system of clause XIV, wherein said sensor comprises a magneto-resistive sensor configured to sense a magnet connected to said housing of said calibration fixture.

XVI. The system of clause XIV, wherein the sensor assembly comprises a mechanical button, an RFID chip, a key handle, a proximity sensor, or a capacitive sensor and is configured to send and receive a signal when said calibration fixture is in the calibration position relative to said surgical handpiece system.

XVII. The system of any of clauses X-XIII wherein the processor is configured to output a nominal size for the surgical screw to be used with said calibration fixture.

XVIII. The system of clause XIV, further comprising a processor either integrated with said surgical handpiece system or integrated with a measurement module removably coupled to said surgical handpiece system, wherein the processor is configured to receive sensor data from said sensor assembly and automatically enter a calibration mode based on the sensor data.

XIX. The system of clause X, wherein the processor is further configured to determine the adjustment based on the nominal size of the surgical screw, a distance from the distal end of the housing/body of said calibration fixture to the distal end of said surgical handpiece system, a length of said slider, and a displacement of the depth measurement extension.

XX. The system of any of clauses I-XIX, wherein the receptacle defined by the housing to receive the surgical screw is offset from the depth measurement extension.

XXI. A system for calibrating a surgical handpiece system capable of determining drill depth to an orthopedic implant set, said system comprising:
  said surgical handpiece system comprising a depth measurement extension and configured to determine a thickness of bone when a drill bit is attached and used to drill through the bone; and
  a calibration fixture configured to engage with said depth measurement extension of said surgical handpiece system to determine an adjustment of the orthopedic implant set, said calibration fixture comprising a housing defining:
    a first receptacle offset from the depth measurement extension and configured to receive a surgical screw of the orthopedic implant set
    a proximal side configured to approach a distal surface of said surgical handpiece system to axially fix the housing of said calibration fixture relative to said surgical handpiece system;
    a second receptacle configured such that the distal end of said receptacle is abuts the distal end of the depth measurement extension, wherein the adjustment is based on displacement of the depth measurement extension.

XXII. A method for calibrating a surgical handpiece system having a depth measurement extension capable of determining drill depth to an orthopedic implant set, said method comprising:
  entering a calibration mode for the surgical handpiece system;
  abutting a housing of a calibration fixture to the surgical handpiece system so that a slider internal to the housing is adjacent to a depth measurement extension of the surgical handpiece system;
  selecting a surgical screw and plate from the orthopedic implant set to be used in an upcoming surgery;
  inserting the surgical screw through the surgical plate and into a receptacle defined by the housing such that the depth measurement extension moves relative to a body of the surgical handpiece system;
  providing to the surgical handpiece system either:
    a nominal size of the surgical screw as provided by the manufacturer of the orthopedic implant set, or
    an adjustment of the surgical screw and plate determined by:
      outputting a displacement by the surgical handpiece, and
      subtracting the displacement output by the surgical handpiece system from the nominal size of the surgical screw;
  using the surgical handpiece system to drill through a bone and obtain a thickness of the bone from displacement of the depth measurement extension; and
  displaying a recommended size for the surgical screw based on the thickness of the bone and the determined adjustment or nominal size of the screw used for calibration.

XXIII. The method of clause XXII, wherein the recommended size is a nominal screw value that is closest to the adjustment plus the thickness of the bone.

XXIV. The method of clause XXII, wherein the surgical handpiece system recommended size is a nominal screw value that is larger than the adjustment plus the thickness of the bone.

XXV. A method for calibrating a surgical handpiece system capable of determining drill depth to an orthopedic implant set, said method comprising:
  identifying a nominal surgical screw size by the surgical handpiece system;
  selecting a surgical screw of the identified nominal size from the orthopedic implant set;
  selecting a surgical plate to be used in an upcoming surgery from the orthopedic implant set;
  abutting a housing of the calibration fixture to the surgical handpiece system so that a depth measurement extension of the surgical handpiece system is inserted into a volume defined by the housing of the calibration fixture;
  inserting the surgical screw through the surgical plate and into a second volume defined by a housing of a calibration fixture;
  depressing the depth measurement extension of the surgical handpiece system with the calibration fixture or surgical screw;

sensing the presence of the calibration fixture with the surgical handpiece system and entering a calibration mode responsive to the sensing;

determining an adjustment based on the nominal surgical screw size and a displacement of the depressed depth measurement extension;

using the surgical handpiece system to drill through a bone and obtain a thickness of the bone; and outputting a recommended size for the surgical screw based on the thickness of the bone and the determined adjustment.

XXVI. The method of clause XXV, wherein determining the adjustment is further based on a distance from a distal end of the calibration fixture to an abutment between the calibration fixture and the surgical handpiece system, a length of a slider mounted within the calibration fixture, and a distance from the abutment to a distal end of the depth measurement extension.

XXVII. The method of any of clauses XXV-XXVI, wherein outputting the recommended size for the surgical screw is only performed when the determined adjustment is less than four millimeters.

XXVIII. The method of any of clauses XXV-XXVII, wherein the identified surgical screw has a nominal size is between 24 and 36 millimeters.

XXIX. The method of any of clauses XXV-XXVIII, wherein the surgical handpiece system displays a recommended size that is closest to the adjustment plus the thickness of the bone.

XXX. The method of any of clauses XXV-XXVIII, wherein the surgical handpiece system displays a recommended size that is larger than the adjustment plus the thickness of the bone.

XXXI. The method of any of clauses XXV-XXX, wherein the sensing step is performed by the surgical handpiece system sensing a magnetic field from a magnet of the calibration fixture.

XXXII. A method for calibrating a surgical handpiece system capable of determining drill depth to an orthopedic implant set, said method comprising:

providing a block having a plate-surface;

selecting the orthopedic implant set for a surgery, wherein the orthopedic implant set contains a depth gauge calibrated to the set;

selecting a surgical plate to be implanted from the orthopedic implant set;

positioning an opening of the surgical plate over an opening of a calibration block and positioning the block so that the block abuts the plate;

inserting the depth gauge through the opening of the calibration block and plate;

subtracting the thickness of the block from the listed value on the depth gauge to obtain an adjustment;

using the surgical handpiece system to drill through a bone and obtain a thickness of the bone; and calculating a recommended size for the surgical screw based on the thickness of the bone and the adjustment.

XXXIII. The method of clause XXXII, further comprising entering the determined adjustment into the surgical handpiece system.

XXXIV. The method of any of clauses XXXII-XXXIII, further comprising the surgical handpiece system identifying a suggested screw size that is closest to the thickness of the bone plus the adjustment.

XXXV. The method of any of clauses XXXII-XXXIII, further comprising the surgical handpiece system identifying a suggested screw that is larger than the thickness of the bone plus the adjustment.

XXXVI. The method of any of clauses XXXII-XXXIII, further comprising selecting a surgical screw based on the adjustment, plus the thickness of the bone, and the area of the patient where a screw is to be implanted.

XXXVII. The method of any of clauses XXXII-XXXIII, further comprising selecting a surgical screw for implantation that is closest to the surgical screw size.

XXXVIII. A surgical handpiece system to determine a suitable screw length for bone fixation with a bone plate that compensates an initial screw length value based on orientation of the surgical handpiece system during a drilling process, said surgical handpiece system comprising:

a surgical handpiece assembly comprising:
a handpiece housing,
a motor disposed within the handpiece housing and configured to generate torque,
a depth measurement extension movably coupled to the handpiece housing,
a coupling chuck coupled to and configured to receive torque from the motor, and
a sensor configured to generate an orientation signal responsive to orientation of the depth measurement extension;

a controller configured to receive the signals from the sensor and determine the suitable screw length for bone fixation based on signals from the sensor.

XXXIX. The surgical handpiece system of clause XXXVIII, wherein the sensor comprises at least one sensor chosen from an accelerometer, a gyroscopic sensor, and a stereoscopic sensor.

XL. The surgical handpiece system of any of clauses XXXVIII-XXXIX, wherein the depth measurement extension defines a measurement axis, with the depth measurement extension movable by a user between a reference orientation where the measurement axis is aligned with a reference axis extending through a hole defined by the bone plate and a drilling orientation where the measurement axis of the depth measurement extension is at an oblique drilling angle relative to the reference axis, and wherein the controller is configured to:

(i) receive the orientation signal from the sensor of the depth measurement extension at the drilling orientation, (ii) determine the drilling angle of the depth measurement extension based on the orientation signal from the sensor, (iii) determine a compensation length responsive to the drilling angle, and (iv) determine a suitable screw length for bone fixation based on the compensation length.

XLI. The surgical handpiece system of clause XL, wherein the sensor comprises a gyroscopic sensor and the orientation signal comprises angular velocity values corresponding to change in orientation of the depth measurement extension as the depth measurement extension moves from the reference orientation to the drilling orientation, and wherein the controller is configured to determine the drilling angle of the depth measurement extension by integrating the angular velocity values over a duration of time, with the duration of time beginning when the reference orientation is established and ending when the drilling orientation is established.

XLII. The surgical handpiece system of any of clauses XL-XLI, further comprising a drill bit coupled to the coupling chuck and configured to receive torque from the motor through the coupling chuck, wherein the depth measurement extension comprises a displacement sensor configured to generate a displacement signal to the controller responsive to displacement of the drill bit during the drilling process, and wherein at least one of the orientations selected from the reference orientation and the drilling orientation is established by the controller (i) receiving the displacement signal, and (ii) determining the drill bit has been displaced relative to the depth measurement extension by a predetermined distance.

XLIII. The surgical handpiece system of clause XLII, wherein the drill bit comprises a drill bit axis and the drill bit axis is aligned with the measurement axis of the depth measurement extension.

XLIV. The surgical handpiece system of any of clauses XL-XLII, further comprising a sensor configured to generate a motor state signal to the controller responsive to a state of the motor, wherein at least one of the orientations selected from the reference orientation and the drilling orientation is established by the controller determining that the state of the motor has changed from an idle state to a running state.

XLV. The surgical handpiece system of clause XLIV, wherein the motor state signal comprises a torque generated by the motor, and wherein the motor does not generate torque in the idle state and the motor generates torque in the running state.

XLVI. The surgical handpiece system of clause XLIV, wherein the motor state signal comprises a rotational speed of the motor, and wherein the motor operates at a rotational speed below a rotational speed threshold in the idle state and the motor operates at another rotational speed above the rotational speed threshold in the running state.

XLVII. The surgical handpiece system of any of clauses XL-XLI, wherein at least one of the orientations selected from the reference orientation and the drilling orientation is established by the controller determining the orientation signals from the sensor of the depth measurement extension have remained constant for a predetermined period of time.

XLVIII. The surgical handpiece system of any of clauses XL-XLI, wherein the surgical handpiece assembly further comprises a user input device operable to generate a first reference signal to the controller to establish that the measurement axis is aligned with the reference axis and to establish the depth measurement extension is in the reference orientation.

XLIX. The surgical handpiece system of clause XLVIII, wherein the drilling orientation is established by operation of the user input device to generate a second reference signal, and wherein the controller (i) receives the second reference signal after receiving the first reference signal, and (ii) determines the depth measurement extension is in the drilling orientation.

L. The surgical handpiece system of any of clauses XL-XLI, wherein the surgical handpiece assembly further comprises a trigger to generate a trigger signal responsive to actuation of the trigger by a user to the controller for operating the motor to generate torque, and wherein at least one of the orientations selected from the reference orientation and the drilling orientation is established by the controller determining the trigger has been actuated by the user.

LI. The surgical handpiece system of any of clauses XL-L, wherein the compensation length is selected using a function dependent on the drilling angle.

LII. The surgical handpiece system of any of clauses XL-L, wherein the compensation length is selected using a look-up table dependent on the drilling angle.

LIII. A surgical handpiece system to determine a suitable screw length for bone fixation with a bone plate that compensates an initial screw length value based on orientation of the surgical handpiece system during a drilling process, said surgical handpiece system comprising:
  a surgical handpiece assembly comprising:
    a handpiece housing,
    a motor disposed within the handpiece housing and configured to generate torque,
    a coupling chuck coupled to and configured to receive torque from the motor, and
    a sensor configured to be coupled to the handpiece housing and configured to generate an orientation signal responsive to orientation of the handpiece housing;
  a controller configured to receive the signals from the sensor and determine the suitable screw length for bone fixation based on signals from the sensor.

LIV. A method of determining a suitable screw length for bone fixation, said method comprising:
  providing a surgical handpiece assembly having a handpiece housing, a motor, and a depth measurement extension defining a measurement axis, the depth measurement extension of the surgical handpiece assembly coupled to a drill bit;
  orienting the depth measurement extension to a reference orientation adjacent a bone plate such that the measurement axis is aligned with a reference axis extending through a hole defined by the bone plate;
  operating a user input device coupled to the surgical handpiece assembly to establish that the measurement axis of the depth measurement extension is aligned with the reference axis;
  orienting the depth measurement extension to a drilling orientation such that the measurement axis is at an oblique angle to the reference axis;
  measuring the oblique angle at the drilling orientation;
  drilling by the drill bit through a proximal cortex of a bone and toward a distal cortex of the bone;
  determining by a controller the suitable screw length for bone fixation based on the oblique angle measurement of the depth measurement extension; and
  displaying the suitable screw length for bone fixation.

LV. The method of clause LIV, wherein the drill bit defines a drill axis that is aligned with the measurement axis, the method further comprising determining the displacement of the drill bit based on relative movement between the depth measurement extension and the drill bit.

LVI. The method of clause LV, further comprising determining by the controller the oblique angle after the drill bit has been displaced a predetermined depth into the bone through the proximal cortex.

LVII. A method of determining a suitable screw length for bone fixation, said method comprising:
  providing a surgical handpiece assembly having a handpiece housing, a motor, a depth measurement extension, and a drill bit;
  drilling through a proximal cortex of a bone and toward a distal cortex of the bone;
  measuring a bore depth in the bone;
  determining the suitable screw length for bone fixation based on the measured bore depth and an oblique drilling factor; and
  displaying the suitable screw length for bone fixation.

LVIII. The method of clause LVII, wherein the surgical handpiece assembly further comprises a user input device, the method further comprising operating the user input device to select the oblique drilling factor before the controller determines the suitable screw length for bone fixation.

LVIX. The method of any of clauses LVII-LVIII, wherein the depth measurement extension defines a measurement axis and the drill bit defines a drill axis that is aligned with the measurement axis, the method further comprising measuring the bore depth by determining the displacement of the drill bit relative to the depth measurement extension.

LX. A measurement module configured to be coupled to a surgical handpiece assembly and configured to engage a calibration fixture to calibrate an orthopedic implant set, said measurement module comprising:
 a housing;
 a depth measurement extension movably coupled to the housing;
 a displacement sensor assembly coupled to the distal portion of the housing and configured to generate a displacement signal responsive to movement of the depth measurement extension relative to the housing;
 a presence sensor coupled to the distal portion of the housing and configured to generate a presence signal responsive to a presence of an emitter coupled to the calibration fixture; and
 a controller configured to receive the signals from the displacement sensor assembly and the presence sensor;
 wherein the controller is configured to receive the signal from the presence sensor and determine the calibration fixture is engaging the distal portion of the housing to operate the surgical handpiece system in a calibration mode such that the displacement signal received from the displacement sensor assembly while surgical handpiece system is in the calibration mode is used to determine an adjustment of the orthopedic implant set, with the controller configured to store the adjustment in memory.

LXI. A calibration assembly for calibrating a surgical handpiece system having a depth measurement extension to an orthopedic implant set, said calibration assembly comprising:
 a housing having a body, the body defining a first opening at a distal end of the body, a second opening at a proximal end of the body, and a lumen extending through the body in fluid communication with the first and second openings, with the lumen configured to receive a surgical screw of the orthopedic implant set through the first opening, and with the lumen configured to receive the depth measurement extension of the surgical handpiece system through the second opening, and the proximal end of the housing configured to engage a distal surface of the surgical handpiece system for axially constraining the housing relative to the surgical handpiece system; and
 a slider movably coupled to the housing and configured to move axially relative to the housing at least partially within the lumen, the slider has a proximal surface configured to engage with the depth measurement extension of the surgical handpiece system and a distal surface configured to engage with the surgical screw, with the slider configured to be displaced within the lumen by the surgical screw when the surgical screw is received within the first opening;
 wherein an adjustment of the orthopedic implant set is determined based on displacement of the slider.

What is claimed is:

1. A surgical handpiece system to determine a suitable screw length for bone fixation with a bone plate that compensates an initial screw length value based on orientation of the surgical handpiece system during a drilling process, said surgical handpiece system comprising:
 a surgical handpiece assembly comprising:
  a handpiece housing,
  a motor disposed within the handpiece housing and configured to generate torque,
  a depth measurement extension movably coupled to the handpiece housing, and wherein the depth measurement extension defines a measurement axis, with the depth measurement extension movable by a user between a reference orientation where the measurement axis is aligned with a reference axis extending through a hole defined by the bone plate and a drilling orientation where the measurement axis of the depth measurement extension is at an oblique drilling angle relative to the reference axis, and
  a sensor configured to generate an orientation signal responsive to orientation of the depth measurement extension;
 a drill bit configured to be coupled to and receive torque from the motor of the surgical handpiece assembly; and
 a processor configured to receive the signals from the sensor and determine the suitable screw length for bone fixation based on signals from the sensor,
 wherein the processor is configured to:
  (i) receive the orientation signal from the sensor of the depth measurement extension at the drilling orientation,
  (ii) determine the drilling angle of the depth measurement extension based on the orientation signal from the sensor,
  (iii) determine a compensation length responsive to the drilling angle, and
  (iv) determine a suitable screw length for bone fixation based on the compensation length.

2. The surgical handpiece system of claim 1, wherein the sensor comprises at least one sensor chosen from an accelerometer, a gyroscopic sensor, and a stereoscopic sensor.

3. The surgical handpiece system of claim 1, wherein the sensor comprises a gyroscopic sensor and the orientation signal comprises angular velocity values corresponding to change in orientation of the depth measurement extension as the depth measurement extension moves from the reference orientation to the drilling orientation, and wherein the processor is configured to determine the drilling angle of the depth measurement extension by integrating the angular velocity values over a duration of time, with the duration of time beginning when the reference orientation is established and ending when the drilling orientation is established.

4. The surgical handpiece system of claim 1, wherein the depth measurement extension comprises a displacement sensor configured to generate a displacement signal to the processor responsive to displacement of the drill bit during the drilling process, and wherein at least one of the orientations selected from the reference orientation and the drilling orientation is established by the processor (i) receiving the displacement signal, and (ii) determining the drill bit has been displaced relative to the depth measurement extension by a predetermined distance.

5. The surgical handpiece system of claim 1, further comprising a sensor configured to generate a motor state signal to the processor responsive to a state of the motor, wherein at least one of the orientations selected from the reference orientation and the drilling orientation is established by the processor determining that the state of the motor has changed from an idle state to a running state.

6. The surgical handpiece system of claim 5, wherein the motor state signal comprises a torque generated by the motor, and wherein the motor does not generate torque in the idle state and the motor generates torque in the running state.

7. The surgical handpiece system of claim 5, wherein the motor state signal comprises a rotational speed of the motor, and wherein the motor operates at a rotational speed below a rotational speed threshold in the idle state and the motor operates at another rotational speed above the rotational speed threshold in the running state.

8. The surgical handpiece system of claim 1, wherein at least one of the orientations selected from the reference orientation and the drilling orientation is established by the processor determining the orientation signals from the sensor of the depth measurement extension have remained constant for a predetermined period of time.

9. The surgical handpiece system of claim 1, wherein the surgical handpiece assembly further comprises a user input device operable to generate a first reference signal to the processor to establish that the measurement axis is aligned with the reference axis and to establish the depth measurement extension is in the reference orientation.

10. The surgical handpiece system of claim 9, wherein the drilling orientation is established by operation of the user input device to generate a second reference signal, and wherein the processor (i) receives the second reference signal after receiving the first reference signal, and (ii) determines the depth measurement extension is in the drilling orientation.

11. The surgical handpiece system of claim 1, wherein the surgical handpiece assembly further comprises a trigger to generate a trigger signal responsive to actuation of the trigger by a user to the processor for operating the motor to generate torque, and wherein at least one of the orientations selected from the reference orientation and the drilling orientation is established by the processor determining the trigger has been actuated by the user.

12. The surgical handpiece system of claim 1, wherein the compensation length is selected using a function dependent on the drilling angle.

13. The surgical handpiece system of claim 1, wherein the compensation length is selected using a look-up table dependent on the drilling angle.

14. The surgical handpiece system of claim 1, wherein the drill bit comprises a drill bit axis and the drill bit axis is aligned with the measurement axis of the depth measurement extension.

15. A surgical handpiece system to determine a suitable screw length for bone fixation with a bone plate that compensates an initial screw length value based on orientation of the surgical handpiece system during a drilling process, said surgical handpiece system comprising:
  a surgical handpiece assembly comprising:
    a handpiece housing,
    a motor disposed within the handpiece housing and configured to generate torque,
    a depth measurement extension movably coupled to the handpiece housing, the depth measurement extension defining a measurement axis, with the depth measurement extension being movable by a user between a reference orientation where the measurement axis is aligned with a reference axis extending through a hole defined by the bone plate and a drilling orientation where the measurement axis of the depth measurement extension is at an oblique drilling angle relative to the reference axis,
    a coupling chuck coupled to and configured to receive torque from the motor, and
    a sensor configured to generate an orientation signal responsive to orientation of the depth measurement extension; and
  a processor configured to receive the signals from the sensor and determine the suitable screw length for bone fixation based on signals from the sensor,
  wherein the processor is configured to:
    (i) receive the orientation signal from the sensor of the depth measurement extension at the drilling orientation,
    (ii) determine the drilling angle of the depth measurement extension based on the orientation signal from the sensor,
    (iii) determine a compensation length responsive to the drilling angle, and
    (iv) determine a suitable screw length for bone fixation based on the compensation length.

16. A method of determining a suitable screw length for bone fixation, said method comprising:
  providing a surgical handpiece assembly having a handpiece housing, a motor, and a depth measurement extension defining a measurement axis, the depth measurement extension of the surgical handpiece assembly coupled to a drill bit;
  orienting the depth measurement extension to a reference orientation adjacent a bone plate such that the measurement axis is aligned with a reference axis extending through a hole defined by the bone plate;
  operating a user input device coupled to the surgical handpiece assembly to establish that the measurement axis of the depth measurement extension is aligned with the reference axis;
  orienting the depth measurement extension to a drilling orientation such that the measurement axis is at an oblique angle to the reference axis;
  measuring the oblique angle at the drilling orientation;
  drilling, by the drill bit, through a proximal cortex of a bone and toward a distal cortex of the bone;
  determining, by a processor, the suitable screw length for bone fixation based on the oblique angle measurement of the depth measurement extension; and
  displaying the suitable screw length for bone fixation.

17. The method of claim 16, further comprising the step of determining the displacement of the drill bit based on relative movement between the depth measurement extension and the drill bit.

18. The method of claim 17, further comprising the step of determining the oblique angle after the drill bit has been displaced a predetermined depth into the bone through the proximal cortex.

* * * * *